US009250252B2

(12) United States Patent
Krishnan et al.

(10) Patent No.: US 9,250,252 B2
(45) Date of Patent: Feb. 2, 2016

(54) INTRACELLULAR PH SENSOR USING NUCLEIC ACID ASSEMBLIES

(75) Inventors: Yamuna Krishnan, Bangalore (IN); Satyajit Mayor, Bangalore (IN); Souvik Modi, Bangalore (IN)

(73) Assignee: NATIONAL CENTRE FOR BIOLOGICAL SCIENCES, Bangalore (IN)

( * ) Notice: Subject to any disclaimer, the term of this patent is extended or adjusted under 35 U.S.C. 154(b) by 516 days.

(21) Appl. No.: 12/474,550

(22) Filed: May 29, 2009

(65) Prior Publication Data

US 2010/0304370 A1  Dec. 2, 2010

(51) Int. Cl.
  *C12Q 1/68* (2006.01)
  *G01N 33/84* (2006.01)
  *C07H 21/04* (2006.01)

(52) U.S. Cl.
  CPC ............ *G01N 33/84* (2013.01); *A01K 2207/05* (2013.01); *A01K 2227/703* (2013.01); *A01K 2267/0393* (2013.01); *C12Q 1/68* (2013.01); *C12Q 1/6818* (2013.01); *C12Q 1/6876* (2013.01)

(58) Field of Classification Search
  None
  See application file for complete search history.

(56) References Cited

U.S. PATENT DOCUMENTS

| 5,625,051 A | 4/1997 | Gehring et al. |
| 6,696,285 B1 | 2/2004 | Mills et al. |
| 2007/0190543 A1 | 8/2007 | Livak |
| 2009/0042205 A1 | 2/2009 | Didenko |

FOREIGN PATENT DOCUMENTS

| WO | WO 2008/017507 | * | 2/2008 |
| WO | WO-2008/017507 A2 | | 2/2008 |

OTHER PUBLICATIONS

Modi, S. et al. A DNA nanomachine that maps spatial and temporal pH changes inside living cells. Nature Nanotechnology, pp. 1-6, published online Apr. 6, 2009.*
Murphy, Robert F. et al. Endosome pH measured in single cells by dual fluorescence flow cytometry: rapid acidification of insulin to pH 6. The J Cell Biology, vol. 98, 1984, pp. 1757-1762.*
Ohmichi, t et al. DNA-based biosensor for monitoring pH in vitro and in living cells. Biochemistry, vol. 44, pp. 7125-7130, 2005.*
Liu, D. et al. A proton-fuelled DNA nanomachine. Angew. Chem. Int. Ed., vol. 42, p. 5734-5736, 2003.*
Ai, Hui-wang et al., "Fluorescent Protein FRET Pairs for Ratiometric Imaging of Dual Biosensors," *Nature Methods*, vol. 5, No. 5, pp. 401-403, May 2008.

Alberti, Patrizia et al., "DNA Duplex-quadruplex Exchange as the Basis for a Nanomolecular Machine," *PNAS*, vol. 100, No. 4, pp. 1569-1573, Feb. 18, 2003.
Allan, Victoria J. et al., "Membrane Motors," *Current Opinion in Cell Biology*, vol. 11, pp. 476-482, 1999.
Altan, Nihal et al., "Defective Acidification in Human Breast Tumor Cells and Implications for Chemotherapy," *J. Exp. Med.*, vol. 187, No. 10, pp. 1583-1598, May 18, 1998.
Bath, Jonathan et al., "DNA Nanomachines," *Nature Nanotechnology*, vol. 2, pp. 275-284, May 2007.
Benenson, Yaakov et al., "An Autonomous Molecular Computer for Logical Control of Gene Expression," *Nature*, vol. 429, pp. 423-429, May 27, 2004.
Beyer, Stefan et al., "A modular DNA signal translator for the controlled release of a protein by an aptamer," *Nucleic Acids Research*, vol. 34, No. 5, 2006, pp. 1581-1587.
Bhatia, Dhiraj et al., "Icosahedral DNA Nanocapsules by Modular Assembly," *Angew. Chem. Int. Ed.*, 2009, vol. 48, pp. 1-5.
Brasuel, Murphy et al., Fluorescent Nanosensors for Intracellular Chemical Analysis: Decyl Methacrylate Liquid Polymer Matrix and Ion-Exchange-Based Potassium PEBBLE Sensors with Real-Time Application to Viable Rat C6 Glioma Cells, *Anal. Chem.*, vol. 73, No. 10, May 15, 2001, pp. 2221-2228.
Chakraborty, Saikat et al., Kinetic hybrid i'motifs: Intercepting DNA with RNA to form a $DNA_2$-$RNA_2$ i-motif, *Biochimie*, vol. 90, 2008, pp. 1088-1095.
Chakraborty, Saikat et al., "The poly dA helix: a new structural motif for high performance DNA-based molecular switches," *Nucleic Acids Research*, Mar. 11, 2009, pp. 1-8.
Clark, Heather A. et al., "Optical Nanosensors for Chemical Analysis inside Single Living Cells. 2. Sensors for pH and Calcium and the Intracellular Application of PEBBLE Sensors," *Analytical Chemistry*, vol. 71, No. 21, Nov. 1, 1999, pp. 4837-4843.
Disbrow, Gary L. et al., "Endoplasmic Reticulum-Localized Human Papillomavirus Type 16 E5 Protein Alters Endosomal pH but Not trans-Golgi pH," *Journal of Virology*, vol. 79, No. 9, May 2005, pp. 5839-5846.
Downey, Gregory P. et al., "Phagosomal Maturation, Acidification, and Inhibition of Bacterial Growth in Nanphagocytic Cells Transfected with FcγRIIA Receptors," *The Journal of Biological Chemistry*, vol. 274, No. 40, Oct. 1, 1999, pp. 28436-28444.
Gehring, Kalle et al., "A tetrameric DNA structure with protonated cytosine-cytosine base pairs," *Nature*, vol. 363, pp. 561-565, Jun. 10, 1993.

(Continued)

*Primary Examiner* — Prabha Chunduru
(74) *Attorney, Agent, or Firm* — Foley & Lardner LLP

(57) ABSTRACT

Disclosed are nucleic acid-based sensors for measuring the pH of a sample, including cells, regions thereof, and whole organisms. The sensor includes an I-switch that is triggered by protons, and which functions as a FRET-based pH sensor inside living cells and organisms. Also disclosed are compositions and methods for measuring the pH of a specific region of a cell, such as vesicles, the nucleus, mitochondrial matrix, or the Golgi lumen.

17 Claims, 18 Drawing Sheets

(56) References Cited

OTHER PUBLICATIONS

Ghodke, Harshad B. et al., "The I-Tetraplex Building Block: Rational Design and Controlled Fabrication of Robust 1D DNA Scaffolds through Non-Watson-Crick Interactions," *Angew. Chem. Int. Ed.*, vol. 46, pp. 2646-2649, 2007.
Grant, Robert L. et al., "Ratiometric Measurement of Intracellular pH of Cultured Cells with BCECF in a Fluorescence Multi-Well Plate Reader," *In Vitro Cell Dev. Biol.*, vol. 33, Apr. 1997, pp. 256-260.
Griesbeck, Oliver, "Fluorescent proteins as sensors for cellular functions," *Current Opinion in Neurobiology*, vol. 14, 2004, pp. 636-641.
Kneen, Malea et al., "Green Fluorescent Protein as a Noninvasive Intracellular pH Indicator," *Biophysical Journal*, vol. 74, Mar. 1998, pp. 1591-1599.
Koo, Mei K. et al., "Simultaneous Analysis of Steady-State Intracellular pH and Cell Morphology by Automated Laser Scanning Cytometry," *International Society for Analytical Cytology, Cytometry Part A*, 2007, pp. 87-93.
Liedl, Tim et al., "Switching the Conformation of a DNA Molecule with a Chemical Oscillator," *American Chemical Society, Nano Letters*, vol. 5, No. 10, 2005, pp. 1894-1898.
Lin, Jie, "Recent development and applications of optical and fiber-optic pH sensors," *Trends in Analytical Chemistry*, vol. 19, No. 9, 2000, pp . 541-552.
Liu, Juewen et al., "A Colorimetric Lead Biosensor Using DNAzyme-Directed Assemble of Gold Nanoparticles." *American Chemical Society*, vol. 125, No. 22, 2003, pp. 6642-6643.
Liu, Dongsheng et.al., "A Proton-Fuelled DNA Nanomachine," *Angew Chem. Int. Ed.*, vol. 42, pp. 5734-5736, 2003.
Mao, Chengde, et al., "A nonomechanical device based on the B-Z transition of DNA", *Nature*, vol. 397, pp. 144-146, Jan. 14, 1999.
Matsuyama, S. et al., "Mitochondria-dependent apoptosis and cellular pH regulation," *Cell Death and Differentiation*, vol. 7, pp. 1155-1165, 2000.
Miesenböck, Gero et al., "Visualizing secretion and synaptic transmission with pH-sensitive green fluorescent proteins," *Nature*, vol. 394, pp. 192-195, Jul. 9, 1998.
Modi, Souvik et al., "The PNA-DNA hybrid I-motif: implications for sugar-sugar contacts in i-motif tetramerization," *Nucleic Acids Research*, vol. 34, No. 16, pp. 4354-4363, 2006.
Modi, Souvik et al., "A DNA nanomachine that maps spatial and temporal pH changes inside living cells," *Nature Nanotechnology*, pp. 1-6, published online: Apr. 6, 2009.
Murphy, Robert F. et al., "Endosome pH Measured in Single Cells by Dual Fluorescence Flow Cytometry: Rapid Acidification of Insulin to pH 6," *The Journal of Cell Biology*, vol. 98, May 1984, pp. 1757-1762.
Ohkuma, Shoji et al., "Fluorescence probe measurement of the intralysosomal pH in living cells and the perturbation of pH by various agents", *Proc. Natl. Acad, Sci. USA*, vol. 75, No. 7, pp. 3327-3331, Jul. 1978.
Overly, Caroline C. et al., "Quantitative measurement of intraorganelle pH in the endosomal-lysosomal pathway in neurons by using ratiometric imaging with pyranine", *Proc. Natl. Acad, Sci. USA*, vol. 92, pp. 3156-3160, Apr. 1995.
Paul, Alexis et al., "Combining G-Quadruplex Targeting Motifs on a Single Peptide Nucleic Acid Scaffold: A Hybrid (3+1) PNA-DNA Bimolecular Quadruplex," *Chem. Eur. J.*, vol. 14, pp. 8682-8689, 2008.
Pitchiaya, Sethuramasundaram et al., "First blueprint, now bricks: DNA as construction material on the nanoscale," *Chem. Soc. Rev.*, vol. 35, pp. 1111-1121, 2006.
Roos, Albert et al., "Intracellular pH," *Physiological Reviews*, vol. 61, No. 2, pp. 296-434, Apr. 1981.
Shih, William, "Dynamic DNA," *Nature Materials*, vol. 7, pp. 98-100, Feb. 2008.
Sipe, David M. et al., "High-resolution kinetics of transferrin acidification in BALB/c 3T3 cells: Exposure to pH 6 followed by temperature-sensitive alkalinization during recycling," *Proc. Natl. Acad. Sci. USA*, vol. 84, pp. 7119-7123, Oct. 1987.

Srivastava, Jyoti et al., "Intracellular pH Sensors: Design Principles and Functional Significance," *Physiology*, vol. 22, pp. 30-39, Feb. 2007.
Tan, Weihong et al., "Submicrometer Intracellular Chemical Optical Fiber Sensors," *Science*, vol. 258, pp. 778-781, Oct. 30, 1992.
Thomas, John A. et al., "Intracellular pH Measurements in Ehrlich Ascites Tumor Cells Utilizing Spectroscopic Probes Generated in Situ," *Biochemistry*, vol. 18, No. 11, pp. 2210-2218, 1979.
Walker, David J. et al., "Simultaneous Measurement of Intracellular pH adn $K^+$ or $NO_3^-$ in Barley Root Cells Using Triple-Barreled, Ion-Selective Microelectrodes" *Plant Physiol.* vol. 108, pp. 743-751, 1995.
Xue, Lin et al., "A ratiometric fluorescent sensor with a large Stokes shift for imaging zinc ions in living cells," *Chem. Commun.*, pp. 1061-1063, 2009.
Yin, Peng et al., "Programming biomolecular self-assembly pathways," *Nature*, vol. 451, pp. 318-323, Jan. 17, 2008.
Yurke, Bernard et al., "A DNA-fuelled molecular machine made of DNA," *Letters to Nature*, vol. 406, pp. 605-608, Aug. 10, 2000.
Berger, M., "Synthetic DNA nanomachines go to work inside living cells", Apr. 9, 2009, accessed at http://www.nanowerk.com/spotlight/spotid=10028.php, downloaded Jun. 15, 2012, 3 pages, Nanowerk LLC.
Cross, et al., "Nanomechanical analysis of cells from cancer patients", Nature Nanotechnology, (2007), vol. 2, pp. 780-783, Nature Publishing Group.
Kim, et al., "Two-Photon Fluorescent Probes for Acidic Vesicles in Live Cells and Tissue", Angewandte Chemie, (2008), vol. 120, pp. 2263-2266, Wiley-VCH Verlag GmbH & Co.
Lee, et al., "A Protein Nanocarrier from Charge-Conversion Polymer in Response to Endosomal pH", Journal of the American Chemical Society, (2007), vol. 129, No. 17, pp. 5362-5363, American Chemical Society.
Li, et al., "Target-Responsive Structural Switching for Nucleic Acid-Based Sensors", Accounts of Chemical Research, (2010), vol. 43, No. 5, pp. 631-641, American Chemical Society.
Liedl, T., "DNA-based nanodevices", Nanotoday, (2007), vol. 2, No. 2, pp. 36-41, Elsevier.
Mavroidis, M., "Nano-Robotics in Medical Applications: From Science Fiction to Reality", Powerpoint presentation accessed at http://www.bionano.neu.edu/NanoRobotics_in_Medicine.pdf, linked as "IROS 2008 NanoRobotics Workshop", downloaded Apr. 30, 2013, 24 pages, Northeastern University.
Nicolau, et al., "Liposomes as carriers for in vivo gene transfer and expression", Methods in Enzymology, (1987), vol. 149, pp. 157-176, Elsevier.
Wong, et al., "Appearance of beta-lactamase activity in animal cells upon liposome-mediated gene transfer", Gene, (1980), vol. 10, pp. 87-94, Elsevier.
Anderson, R. G., et al., "Visualization of acidic organelles in intact cells by electron microscopy," Proceedings of the National Academy of Sciences of the United States of America, vol. 81, No. 15, pp. 4838-4842 (Aug. 1, 1984).
Balzani, V., et al., "Autonomous Artificial Nanomotor Powered by Sunlight," Proceedings of the National Academy of Sciences of the United States of America, vol. 103, No. 5, pp. 1178-1183 (Jan. 31, 2006).
Eelkema, R., et al., "Molecular machines: Nanomotor rotates microscale objects," Nature, vol. 440, No. 7081, p. 163 (Mar. 9, 2006).
Guha, A., et al., "Shibire mutations reveal distinct dynamin-independent and -dependent endocytic pathways in primary cultures of Drosophila hemocytes," Journal of Cell Science, vol. 116, Pt. 16, pp. 3373-3386 (Aug. 15, 2003).
Mukherjee, S., et al., "Endocytosis," Physiological Reviews vol. 77, No. 3, pp. 759-803 (Jul. 1, 1997).
Simchowitz, L., and Cragoe Jr. E.J. "Regulation of human neutrophil chemotaxis by intracellular pH," Journal of Biological Chemistry, vol. 261, No. 14, pp. 6492-6500 (May 15, 1986).
Stojanovic, M. N., et al., "Deoxyribozyme-based logic gates," Journal of the American Chemical Society, vol. 124, No. 14, pp. 3555-3561 (Mar. 14, 2002).
Stryer, L., and Haugland, R. P., "Energy transfer: a spectroscopic ruler," Proceedings of the National Academy of Sciences of the United States of America, vol. 58, No. 2, pp. 719-726 (Aug. 1967).

* cited by examiner

Coelomocytes

SEQUENCE LISTING

```
<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ccccaacccc aatacatttt acgcctggtg cc                                     32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccgaccgcag gatcctataa aaccccaacc cc                                     32

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 3
ttataggatc ctgcggtcgg aggcaccagg cgtaaaatgt a                          41

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccccaacccc aatacatttt acgcctggtg cc                                    32

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ccccaacccc aatacatttt acgcctggtg cc                                    32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccgaccgcag gatcctataa aaccccaacc cc                                    32

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattatagga tcctgcggtc ggaggcacca ggcgtaaaat gta                        43

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: a, t or g
<220> FEATURE:
<221> NAME/KEY: modified_base
<222> LOCATION: (9)..(10)
<223> OTHER INFORMATION: a, t or g
<220> FEATURE:
<221> NAME/KEY: modified_base
<222> LOCATION: (14)..(15)
<223> OTHER INFORMATION: a, t or g
```

```
<400> SEQUENCE: 8 cccnnccnn cccnn                                              15
```

INTRACELLULAR PH SENSOR USING NUCLEIC ACID ASSEMBLIES

TECHNICAL FIELD

This disclosure relates generally to compositions and methods for measuring the pH of a sample. More particularly, the disclosure relates to nucleic acid-based sensors for measuring the pH of a biological sample, such as cells, regions of cells, tissues, and whole organisms.

BACKGROUND

Cellular metabolism refers to the orchestration of the chemical and enzymatic reactions that constitute the life process of a cell. These reactions include a vast number of different chemical and enzymatic reactions, relating to the growth and maintenance of the cell. A cell carries out a variety of functions, such as DNA replication, DNA transcription, RNA translation, digestion of macromolecules, construction of macromolecules, and monitoring of the extracellular and intracellular conditions. These chemical and enzymatic reactions occur simultaneously within an active cell. Moreover, these reactions do not take place in isolation; rather the pace of each reaction is regulated, in turn, by the product of one or more other reactions. Overall, the organization of cellular metabolism is embedded in a vast network of inter-related cellular reactions. Given this interdependency, it is apparent that analytes that affect one or more aspects of cellular metabolism are likely to manifest their impact on characteristics of the cell, including pH of intracellular compartments. The pH within various cellular compartments is regulated to provide for the optimal activity of many cellular processes. For example, in the secretory pathway, post-translational processing of secretory proteins, the cleavage of prohormones, and the retrieval of escaped luminal endoplasmic reticulum proteins are all pH-dependent.

SUMMARY

The compositions and methods described herein are based on the discovery that a nucleic acid nanomachine or "I-switch" can function as an intracellular pH sensor, which shows reversible changes in fluorescence over physiological pH ranges.

In one aspect, the methods provide for determining the pH of a cell or region thereof comprising: contacting the cell or region thereof with one or more indicators having at least two i-motif forming sequences, wherein one or more first i-motif forming sequences are labeled with a first member of a label pair and one or more second i-motif forming sequences are labeled with a second member of a label pair, wherein the one or more first i-motif forming sequences and the one or more second i-motif forming sequences form one or more i-motifs in response to exposure to one or more pH conditions and the first and second members of the label pair interact; and detecting the presence, absence, or magnitude of a signal from the interacting label pair to determine the pH of the cell or region thereof.

In one embodiment, the at least two i-motif forming sequences form an i-motif having two parallel-stranded $C—H.C^+$ base paired duplexes that are intercalated in an anti-parallel orientation.

In illustrative embodiments, the i-motif is formed under acidic conditions and dissociates under neutral or basic conditions.

In one embodiment, the at least two i-motif forming sequences are present in the same oligonucleotide. In one embodiment, the at least two i-motif forming sequences are present in at least two separate oligonucleotides. In illustrative embodiments, the two separate oligonucleotides are partially complementary to a third oligonucleotide. In one embodiment, the two i-motif forming oligonucleotides have the sequence of SEQ ID NO: 1 and SEQ ID NO: 2. In one embodiment, the third oligonucleotide has the sequence of SEQ ID NO: 3.

In illustrative embodiments, the interacting label pair comprises donor and acceptor moieties. In one embodiment, the interacting label pair is capable of energy transfer. In an illustrative embodiment, the donor moiety is selected from the group consisting of fluorescein, dilithium 4-carboxy-2-(3,6-diamino-4,5-disulfonatoxanthenium-9-yl)benzoate (ALEXA FLUOR™ 488), and 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY™ TMR). In an illustrative embodiment, the acceptor moiety is selected from the group consisting of rhodamine, eosin, erythrosin, (3E)-9-{2-[(4-{[2,5-dioxo-1-pyrrolidinyl)oxy]carbonyl}-1-piperidinyl)sulfonyl]phenyl}-N-methyl-6-[methyl(phenyl)amino]-N-phenyl-3H-xanthen-2-iminium chloride (QSY-7™), (2Z)-3-[6-[5-[[2-[(E)-[(2R,3S,5S,8S,9S,10R,13S,14S,17R)-17-[(2S,3R,4R,5S)-3,4-dihydroxy-5,6-dimethylheptan-2-yl]-2,3-dihydroxy-10,13-dimethyl-1,2,3,4,5,7,8,9,11,12,14,15,16,17-tetradecahydrocyclopenta[alphenanthren-6-ylidene]amino]oxyacetyl]amino]pentylamino]-6-oxohexyl]-2-[(2E,4E)-5-[3,3-dimethyl-5-sulfo-1-(3-sulfopropyl)indol-1-ium-2-yl]penta-2,4-dienylidene]-3-methyl-1-(3-sulfopropyl)indole-5-sulfonic acid (ALEXA FLUOR™ 647), BODIPY™ TMR, 2-[(E,3Z)-3-(1,3-dihydroindol-2-ylidene)prop-1-enyl]-3H-indol-1-ium (CY3™), and 5-(4-{[(2,5-dioxopyrrolidin-1-yl)oxy]carbonyl}phenyl)-2,3,3,7,7,8-hexamethyl-2,3,7,8-tetrahydro-1H-pyrano[3,2-f:5,6-f]diindole-10,12-disulfonic acid (ALEXA FLUOR™ 532).

In illustrative embodiments, the interacting label pair comprises a fluorophore and a quencher. In one embodiment, the fluorophore is selected from the group consisting of: fluorescein, BODIPY™, ALEXA™, EDANS and IAEDANS. In one embodiment, the quencher is selected from the group consisting of Dabcyl, QSY-7™ and a BLACK HOLE™ dye.

In one embodiment, the detecting comprises measuring the magnitude of the signal generated, wherein the magnitude indicates the pH of the cell or region thereof. In one embodiment, wherein the magnitude of the signal changes as the pH varies from pH 5 to 10 or pH 5 to 7.

In illustrative embodiments, the indicator further comprises a tagging moiety for linking the indicator to other biomolecules. In one embodiment, the tagging moiety is biotin and the indicator is linked to other biomolecules by binding to avidin or streptavidin.

In illustrative embodiments, the indicator further comprises one or more of a fusogenic peptide, a membrane-permeabilizing peptide, a sub-cellular localization sequence, or a cell-receptor ligand. In one embodiment, the sub-cellular localization sequence targets the indicator to a region of the cell selected from the group consisting of: the cytosol, the endoplasmic reticulum, the mitochondrial matrix, the chloroplast lumen, the medial trans-Golgi cisternae, the lumen of lysosome, and the lumen of an endosome. In one embodiment, the sub-cellular localization sequence is selected from the group consisting of a receptor ligand, a nuclear localization sequence (NLS), a nuclear export signal (NES), a plasma membrane targeting signal, a histone binding protein, and a nuclear protein. In one embodiment the fusogenic peptide is a peptide of a viral protein derived from a virus selected from the group consisting of an influenza virus, a vesicular stomatitis virus, and an alphavirus. In one embodiment, the fusogenic peptide is a hemagglutinin of an influenza virus or a glycoprotein of a vesicular stomatitis virus.

In one embodiment, the cell is a eukaryotic cell. In an illustrative embodiment, the cell is a mammalian cell.

In another aspect, the disclosure provides a cell transfected with an indicator having at least two i-motif forming sequences, wherein one or more first i-motif forming sequences are labeled with a first member of a label pair and one or more second i-motif forming sequences are labeled with a second member of a label pair, wherein the one or more first i-motif forming sequences and the one or more second i-motif forming sequences form one or more i-motifs in response to exposure to one or more pH conditions and the first and second members of the label pair interact.

In another aspect, the disclosure provides an organism transfected with an indicator having at least two i-motif forming sequences, wherein one i-motif forming sequence is labeled with a first member of an interacting label pair and a second i-motif forming sequence is labeled with a second member of an interacting label pair, wherein an i-motif is formed under one or more pH conditions and the first and second members of the interacting label pair are brought into proximity and interact.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF FIGURES

FIG. 2a shows the normalized Donor/Acceptor (D/A) intensity (ALEXA FLUOR™ 488/ALEXA FLUOR™ 647) ratios inside endosomes, plotted as a function of pH. The intracellular calibration curve is overlayed on the in vitro pH profile. Error bar: Mean of two independent experiments±s.e.m. FIG. 2b is a schematic diagram of the labelling assay. FIG. 2c shows colocalization of the I-switch with endocytic vesicle marker FITC-Dextran. FIG. 2d shows colocalization of endocytosed I-switch with Rab-5-GFP positive endosomes.

FIG. 3a is a pseudocolour D/A map of hemocytes pulsed with I-switch (ALEXA FLUOR™ 488/647) at indicated chase times. FIG. 3b shows histograms of D/A ratios of ~80 individual endosomes after 5 min, 1 h and 2 h chase times. FIG. 3c is a table summarizing endosomal pH variation as a function of time. FIG. 3d shows real-time monitoring of the rate of acidification during endocytosis.

FIG. 7a shows I-switch labeled with ALEXA FLUOR™ 188 and ALEXA FLUOR™ 647. FIG. 7b shows I-switch labeled with BODIPY™ TMR and ALEXA FLUOR™ 647. FIG. 7c shows fluorescence melting experiments on I-switch at pH 5 in order to confirm i-motif formation. FIG. 7d shows a thermal denaturation profile of the I-switch.

FIG. 8a is a graph of lifetime decay of donor only labeled I-switch. FIG. 8b is a graph of lifetime decay of dual labeled (ALEXA FLUOR™ 488/647) I-switch at indicated pH.

FIG. 15d is a chromatogram showing free $Tf_B$ and when $Tf_B$ was added to $I_{B-SA}$ in a 2:1 ratio, a new peak arises due to formation of $I_{B-SA}$-$Tf_B$ FIG. 15e is a chromatogram showing transferrin has a 475 nm absorbance peak and was followed to probe number of bound transferrins on a single $I_{B-SA}$ complex.

DETAILED DESCRIPTION

Figure 1:
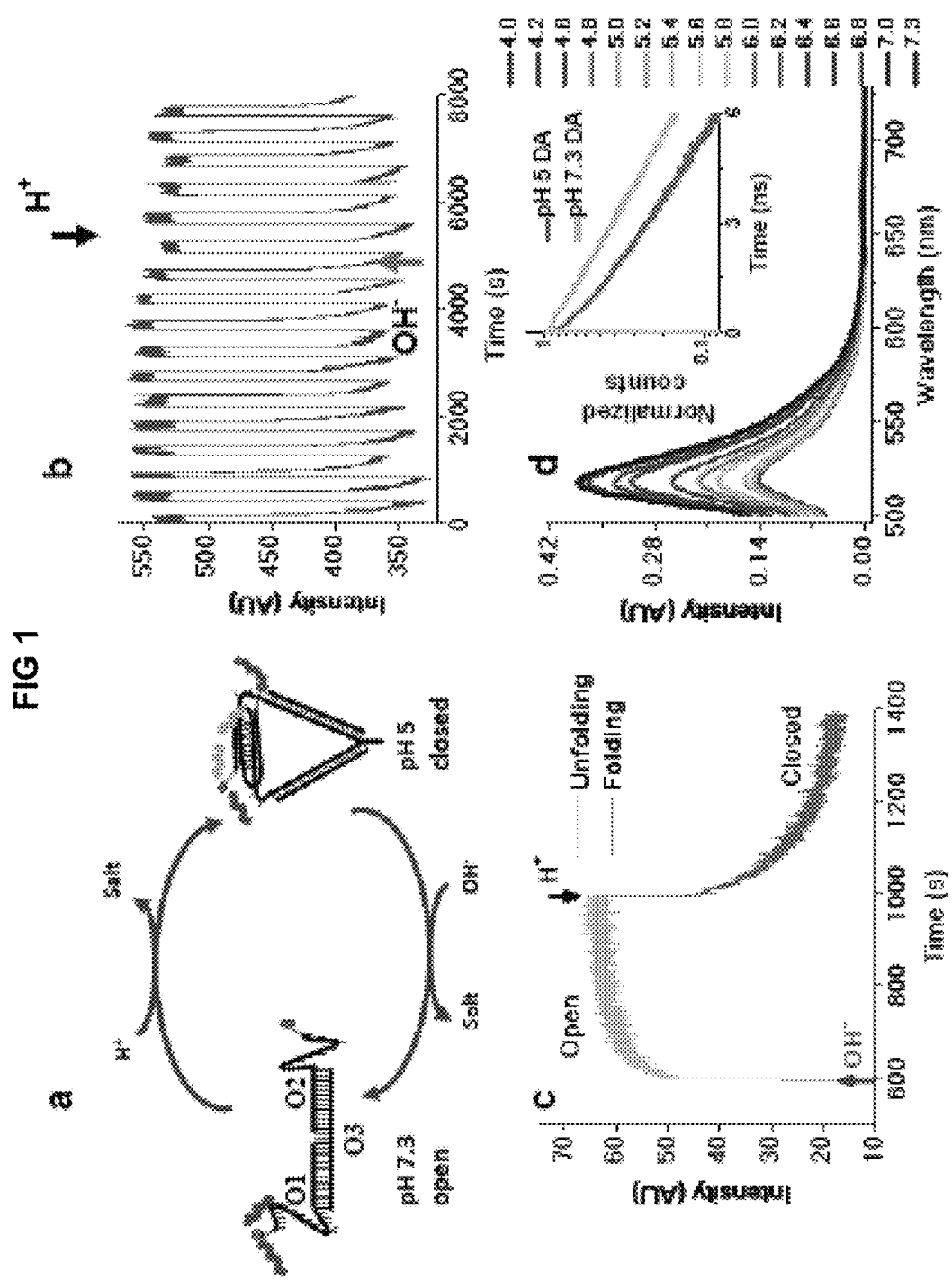
FIG. 1a is a schematic of the working principle of the I-switch in the 'open' state (low FRET) at high pH and in the 'closed' state (high FRET) at low pH.
FIG. 1b is a graph depicting pH cycling of the I-switch in 100 mM KCl showing donor fluorescence intensity upon alternate addition of acid and base corrected for dilution.
FIG. 1c shows representative traces of response time of formation of the open and closed states of the switch in response to pH change.
FIG. 1d shows the fluorescence profile of the ALEXA FLUOR™ 488/647-labeled I-switch (80 nM) in buffers at pH values 4-7.3 in vitro. Inset, Time resolved fluorescence spectra of ALEXA FLUOR™ 488/647 labeled I-switch at pH 5 and pH 7.3.

In the following detailed description, reference may be made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. The present technology is described herein using several definitions, as set forth throughout the specification. As used herein, unless otherwise stated, the singular forms "a," "an," and "the" include plural reference. Thus, for example, a reference to "an oligonucleotide" includes a plurality of oligonucleotide molecules, and a reference to "a nucleic acid" is a reference to one or more nucleic acids.

Nucleic acids, such as DNA and RNA, provide remarkable specificity and versatility in molecular recognition and are therefore excellent nanoscale building blocks to make precisely self assembled nanostructures. DNA nanomachines are synthetic DNA assemblies that switch between defined molecular conformations upon stimulation by external triggers. For example, DNA nanomachines are artificially designed assemblies that change their states in response to an input such as chemical stimuli generated by environmental cues. The present discovery includes an autonomous DNA nanomachine, which is responsive to a specific molecular trigger generated within a living cell. The high-fidelity performance of DNA nanodevices inside living systems illustrates the potential of DNA scaffolds responsive to more complex triggers in sensing, diagnostics and targeted therapies in living systems.

In an illustrative embodiment, this disclosure describes a DNA nanomachine triggered by protons, called an "I-switch" that functions as a pH sensor inside living cells. It is a reporter of pH from about 5 to about 7. In some embodiments, the I-switch has a high dynamic range between pH 5.8-7. The I-switch is easily conjugatable to any protein making it a versatile probe to assay a wide range of biological processes associated with pH change. As shown in the Examples, the I-switch is capable of measuring pH within the molecularly crowded and dynamically changing cellular environment.

In an illustrative embodiment, the I-switch is a DNA nanodevice, having cytosine rich regions, that functions as a sensor for a chemical input, namely protons. Cytosine-rich sequences associate under acidic conditions to form an i-tetraplex, which consists of two parallel-stranded duplexes of protonated cytosine-cytosine base pairs (C—H.C$^+$) that are intercalated in an antiparallel orientation. The DNA assembly is a robust pH triggered nanoswitch with fast response times, sustained efficiency over several cycles and a working cycle that does not generate toxic by-products. This switch functions as a pH sensor for the regime of about pH 5 to about 7, which is suitable for monitoring changes in intracellular pH.

This disclosure demonstrates the successful working of an artificially designed DNA-based pH indicator inside living cells and shows unambiguously that these nanomachines work as efficiently inside cells as in vitro. The by products of a complete cycle for the I-switch are water and salt, which are non-toxic. The I-switch has a pH sensitivity between about pH 5 to 7 or about pH 5.5 to 6.8. The detectable pH range may be adjusted by changing the lengths of the C-rich sequences in the I-switch, or substituting one or more cytosine residues with a modified nucleotide, e.g., 5-methylcytosine. Moreover, the C-rich sequences may be present on a single oligonucleotide (i.e., a unimolecular I-switch) or present on multiple oligonucleotides (i.e., a bimolecular I-switch). As shown in the Examples, unimolecular and bimolecular I-switches exhibit different responses to pH.

Unlike such pH probes, the I-switch is a fluorescence-based sensor which is equally bright at both physiological and acidic pH, is photostable and also offers the advantages of a ratiometric probe. With GFP-based or small molecule pH probes, one is limited by a fixed wavelength, whereas the I-switch is an artificially designed nucleic acid scaffold and can incorporate any appropriate FRET pair. It can therefore be used to simultaneously follow multiple proteins with each protein bearing a distinct FRET pair, thus positioning it as a powerful probe to study crosstalk in complex intracellular sorting or trafficking events. In some embodiments, the response of the I-switch is on timescale of about 1-2 minutes. In other embodiments, the I-switch has a response time of about 10 seconds to about 60 seconds, e.g., about 20 seconds or about 40 seconds. Therefore, the I-switch can be used as a high performance reporter of fine spatio-temporal pH changes associated with biological processes that occur on longer time scales such as pH variations associated with viral infections, phagocytosis, chemotaxis, apoptosis and defective acidification in tumor cells.

In some embodiments, the I-switch can be targeted to various organelles or subcellular regions by utilizing the internalization and transport mechanisms associated with endocytic routes. It is notable that analogous to cellular machines, artificially designed DNA nanomachines are responsive to molecular cues and can be specifically coupled to the cellular environment. Yet, these nanomachines function independently within the crowded cellular milieu. Thus, DNA nanomachine function on the nanoscale can be efficiently transduced to cellular length scales. The robustness and performance of DNA nanomachines inside living systems provides for DNA based cellular devices for sensing, diagnostics and targeted therapies in living systems.

Structure of the I-Switch Oligonucleotides

In illustrative embodiments, the I-switch pH indicator has at least two i-motif forming sequences. As used herein, "nucleic acid," "nucleotide sequence," or "nucleic acid sequence" refer to a nucleotide, oligonucleotide, polynucleotide, or any fragment thereof and to naturally occurring or synthetic molecules. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

As used herein, an "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides.

One nucleic acid sequence may be "complementary" to a second nucleic acid sequence. As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.). Hybridizing under high stringency refers to the above conditions in which washing is performed at 2×SSC, 65° C. (where SSC is 0.15M NaCl, 0.015M sodium citrate, pH 7.2).

In some embodiments, the sequences that make the I-switch indicator for pH sensing form one or more i-motifs. An "i-motif" is a nucleic acid (DNA and/or RNA) containing complex characterized by the presence of cytosine-rich stretches or stretches rich in cytosine derivatives, including two parallel-stranded duplexes in which the cytosines or derivatives thereof form base pairs, and the two duplexes are associated anti-parallel to one another. The pairs of cytosine or derivatives thereof of one duplex are intercalated with those of the other duplex.

The structure of an i-motif differs from that of the usual DNA duplex because the base pairing scheme involves hemi-protonated cytosines which result in the formation of $C.C^+$ base pairs. Specifically, one of the cytosines contained in each pair is protonated. The same interactions may occur using derivatives of cytosine, such as 5-methylcytosine, which include chemical substitutions that enable the cytosine base-pairing scheme to be maintained. The i-motif may also exist as a tetramer formed by the association of two duplexes as described above.

The complex may be synthesized from oligonucleotide sequences including a stretch of at least two, at least three, or at least four consecutive cytosines. By modifying the number of cytosines it is possible to modulate the response time of the I-switch and to the pH sensing range. When more cytosines contribute to the i-motif, the stability of the motif is increased. Moreover, this motif may be formed by the interaction of stretches containing different numbers of cytosines. Furthermore, a cytosine-rich stretch may contain one or two non-cytosine base(s) in between the cytosines. However, this may reduce the stability of the i-motif. The cytosine stretches which comprise the i-motif may belong to different strands of nucleic acids; however, any two of them may also be linked together covalently or non-covalently. Also, any two of them may be part of a single nucleic acid strand wherein they are separated by a stretch of specified bases.

In an illustrative embodiment, the i-motif forming sequences have the general formula $C_nX_2C_nX_2CnX_2$, where C is cytosine and X is adenine, thymine, or guanine, and n is greater than or equal to 3.

In some embodiments, the I-switch includes at least two i-motif forming sequences on at least two separate oligonucleotides. The at least two oligonucleotides may each be at least 4, at least 8, at least 12, at least 16, at least 20, or at least 30 nucleotides in length. In illustrative embodiments, the at least two oligonucleotides may each be no more than about 50 nucleotides in length. In one embodiment, the at least two oligonucleotides, which interact to form the i-motif, may be partially complementary to a third oligonucleotide, which binds the at least two oligonucleotides and keeps them in relatively close proximity within the cell.

In some embodiments, the I-switch includes at least two i-motif forming sequences on a single oligonucleotide. The at least two i-motif forming sequences are spatially separated on the single oligonucleotide, such that they can interact to form an i-motif under the appropriate pH conditions. Interacting labels at or near the opposite ends of the oligonucleotide are brought into proximity, which results in a signal. In order to maintain the separation of the i-motif forming sequences, the single oligonucleotide may be partially complementary to another oligonucleotide. In this way, the i-motif forming oligonucleotide is partnered with another strand that is capable of dissociating when the i-motif is formed. For example, the partner strand may dissociate from the i-motif forming oligonucleotide at high pH due to inherent instability in the duplex. In some embodiments, the duplex is unstable due to the presence of one or more mismatches between the partner strand and the i-motif-forming oligonucleotide.

Minor modifications of the oligonucleotides may result in I-switches which have substantially equivalent or improved activity as compared to the unmodified counterpart oligonucleotides. Such modifications may be deliberate, as by site-directed mutagenesis, or may be spontaneous. All of the oligonucleotides produced by these modifications are included herein as long as the pH-dependent fluorescence of the engineered I-switches still exists.

In some embodiments, the I-switch includes at least one modified base, for instance natural modified bases (such as 6-keto purine, xanthine, 5-methylcytosine or 2-aminopurine) or unnatural modified bases (such as thioguanine or 8-oxoguanine, deazapurine or azapurine), or analogs of bases such as universal bases (such as nebularin, nitroindole or nitropyrrole derivatives). Adjusting the sequence of the oligonucleotides in the I-switch to include at least one modified base may alter the response time of the I-switch or alter the pH range at which the I-switch operates.

Figure 5:
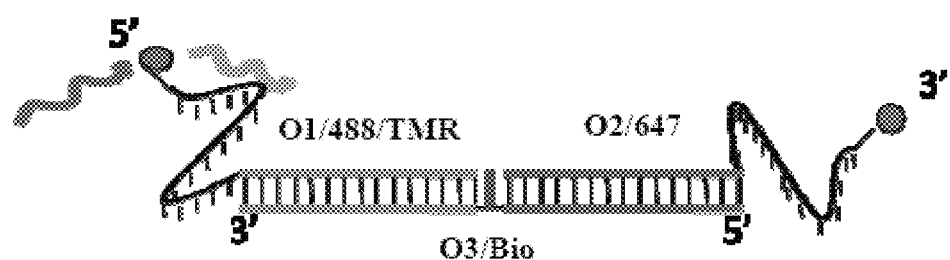
FIG. 5a is a schematic representation of an illustrative DNA nanomachine.

In an illustrative embodiment, the I-switch includes three oligonucleotides, two of which are capable of interacting and forming an i-motif (See FIG. 5). Each of the nucleotides may be about 20-50 nucleotides, about 25-45, about 30-45 or about 30-40 nucleotides in length. For example, the sequences of the oligonucleotides forming the I-switch of FIG. 5, may include those shown in Table 1. In this embodiment, the I-switch is composed of three sequences, O1, O2, and O3. O1 and O2 are partially complementary to O3 to form a linear duplex leaving a gap of at least 1, least 2 two, at least 3, or at least 4 nucleotides, which acts as a fulcrum to facilitate closing and opening of the construct. Under certain pH conditions, such as acidic conditions, the i-motif forming sequences interact to form an i-motif. Interacting labels on the i-motif forming sequences are brought into proximity, which results in a signal. The presence, absence, or magnitude of the signal may then be correlated to pH using known standards. Alternatively, a change in pH may be monitored in real-time to study cellular process.

TABLE 1

Exemplary I-Switch Sequences

| Name | Sequence: | SEQ ID NO |
|---|---|---|
| O1 | 5'-CCCCAACCCCAATACATTTTACGCCTGG<br>TGCC-3' | SEQ ID NO: 1 |
| O2 | 5'-CCGACCGCAGGATCCTATAAAACCCAA<br>CCCC-3' | SEQ ID NO: 2 |
| O3 | 5'-TTATAGGATCCTGCGGTCGGAGGCACCA<br>GGCGTAAAATGTA-3' | SEQ ID NO: 3 |
| O488 | 5'Alexa-488-CCCCAACCCCAATACATTT<br>TACGCCTGGTGCC-3' | SEQ ID NO: 4 |
| O-TMR | 5'-Bodipy-TMR-CCCCAACCCCAATACAT<br>TTTACGCCTGGTGCC-3' | SEQ ID NO: 5 |
| O-647 | 5'-CCGACCGCAGGATCCTATAAAACCCAA<br>CCCC-Alexa-647-3' | SEQ ID NO: 6 |

TABLE 1-continued

Exemplary I-Switch Sequences

| Name | Sequence: | SEQ ID NO |
|---|---|---|
| O3-Bio | 5'-Biotin-AATTATAGGATCCTGCGGTCG<br>GAGGCACCAGGCGTAAAATGTA-3' | SEQ ID NO: 7 |

Labels

In accordance with the methods and compositions disclosed herein, the oligonucleotides may include one or more labels. Oligonucleotides can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, "labels" are chemical or biochemical moieties useful for labeling a nucleic acid. "Labels" include fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide.

In illustrative embodiments, the oligonucleotides may be labeled with a "fluorescent dye" or a "fluorophore." As used herein, a "fluorescent dye" or a "fluorophore" is a chemical group that can be excited by light to emit fluorescence. Some fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following trade names: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-Hydroxy Tryptamine (HAT); 5-ROX (carboxy-X-rhodamine); 6-Carboxyrhodamine 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; ALEXA FLUOR™ 350; ALEXA FLUOR™ 430; ALEXA FLUOR™ 488; ALEXA FLUOR™ 532; ALEXA FLUOR™ 546; ALEXA FLUOR™ 568; ALEXA FLUOR™ 594; ALEXA FLUOR™633; ALEXA FLUOR™ 647; ALEXA FLUOR™ 660; ALEXA FLUOR™ 680; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; BODIPY® 492/515; BODIPY® 493/503; BODIPY® 500/510; BODIPY® 505/515; BODIPY® 530/550; BODIPY® 542/563; BODIPY® 558/568; BODIPY® 564/570; BODIPY® 576/589; BODIPY®

581/591; BODIPY® 630/650-X; BODIPY® 650/665-X; BODIPY® 665/676; BODIPY® FL; BODIPY® FL ATP; BODIPY® Fl-Ceramide; BODIPY® R6G SE; BODIPY® TMR; BODIPY® TMR-X conjugate; BODIPY® TMR-X, SE; BODIPY® TR; BODIPY® TR ATP; BODIPY® TR-X SE; BO-PRO™-1; BO-PRO™-3; Brilliant Sulphoflavin FF; Calcein; Calcein Blue; Calcium Crimson™; Calcium Green; Calcium Orange; Calcofluor White; CASCADE BLUE™; CASCADE YELLOW™; Catecholamine; CCF2 (GENE-BLAZER®); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; CY2™; CY3.18™; CY3.5™; CY3™; CY5.18™; CY5.5™; CY5™; CY7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; FURA RED™; FURA RED™/Fluo-3; Fura-2; Fura-2/BCECF; Genacryl Brilliant Red B; Genacryl Brilliant Yellow 10GF; Genacryl Pink 3G; Genacryl Yellow 5GF; GENE-BLAZER® (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Inodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; LYSO TRACKER® Blue; LYSO TRACKER® Blue-White; LYSO TRACKER® Green; LYSO TRACKER® Red; LYSO TRACKER® Yellow; LYSOSENSOR™ Blue; LYSOSENSOR™ Green; LYSOSENSOR™ Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; OREGON GREEN®; OREGON GREEN™ 488-X; OREGON GREEN™; OREGON GREEN™ 488; OREGON GREEN™ 500; OREGON GREEN™ 514; PACIFIC BLUE™; Pararosaniline (Feulgen); PBFI; PE-Cy5; PE-Cy7; PerCP; PerCP-Cy5.5; PE TEXAS RED® [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7™; Quinacrine Mustard; Red 613 [PE TEXAS RED®]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; SGBFP™; SGBFP™ (super glow BFP); SGBFP™; SGGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SPECTRUMAQUA™; SPECTRUMGREEN™; SPECTRUMORANGE™; SPECTRUMRED™; SPQ (6-methoxy-N-(3-sulfopropyl)quinolinium); Stilbene; Sulphorhodamine B can C; Sulphorhodamine G Extra; SYTO® 11; SYTO® 12; SYTO® 13; SYTO® 14; SYTO® 15; SYTO® 16; SYTO® 17; SYTO® 18; SYTO® 20; SYTO® 21; SYTO® 22; SYTO® 23; SYTO® 24; SYTO® 25; SYTO® 40; SYTO® 41; SYTO® 42; SYTO® 43; SYTO® 44; SYTO® 45; SYTO® 59; SYTO® 60; SYTO® 61; SYTO® 62; SYTO® 63; SYTO® 64; SYTO® 80; SYTO® 81; SYTO® 82; SYTO® 83; SYTO® 84; SYTO® 85; SYTOX® BLUE; SYTOX® GREEN; SYTOX® ORANGE; TET™; Tetracycline; Tetramethylrhodamine (TRITC); TEXAS RED™; TEXAS RED-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO®-1; TO-PRO®-3; TO-PRO®-5; TOTO®-1; TOTO®-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO®-1; YO-PRO®-3; YOYO®-1; YOYO®-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides and nucleotides of the disclosed compositions and methods may be labeled with a quencher. Quenching may include dynamic quenching (e.g., by FRET), static quenching, or both. Illustrative quenchers may include Dabcyl. Illustrative quenchers may also include dark quenchers, which may include BLACK HOLE QUENCHER® dyes (e.g., BHQ®-0, BHQ®-1, BHQ®-2, and BHQ®-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

In some situations, it may be useful to include interactive labels on two or more oligonucleotides with due consideration given for maintaining an appropriate spacing of the labels on the oligonucleotides to permit the separation of the labels during a conformational change in the I-switch. One type of interactive label pair is a quencher-dye pair, which may include a fluorophore and a quencher. The ordinarily skilled artisan can select a suitable quencher moiety that will quench the emission of the particular fluorophore. In an illustrative embodiment, the Dabcyl quencher absorbs the emission of fluorescence from the fluorophore moiety.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are known in the art and may include fluorophores and quenchers described herein such as Fluorescein/Tetramethylrhodamine, IAEDANS/Fluorescein (Molecular Probes, Eugene, Oreg.), EDANS/Dabcyl, Fluorescein/Fluorescein (Molecular Probes, Eugene, Oreg.), BODIPY® FL/BODIPY® FL (Molecular Probes, Eugene, Oreg.), BODIPY® TMR/ALEXA FLUOR™ 647, ALEXA FLUOR™ 488/ALEXA FLUOR™ 647, and Fluorescein/QSY7™.

The labels can be conjugated to the oligonucleotides directly or indirectly by a variety of techniques. Depending upon the precise type of label used, the label can be located at the 5' or 3' end of the oligonucleotide, located internally in the oligonucleotide's nucleotide sequence, or attached to spacer arms extending from the oligonucleotide and having various sizes and compositions to facilitate signal interactions. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite.

Oligonucleotides may also incorporate oligonucleotide functionalizing reagents having one or more sulfhydryl, amino or hydroxyl moieties into the oligonucleotide sequence. For example, 5' phosphate group can be incorporated as a radioisotope by using polynucleotide kinase and $[\gamma^{32}P]ATP$ to provide a reporter group. Biotin can be added to the 5' end by reacting an aminothymidine residue, introduced during synthesis, with an N-hydroxysuccinimide ester of biotin. Labels at the 3' terminus, for example, can employ polynucleotide terminal transferase to add the desired moiety, such as for example, cordycepin, $^{35}S$-dATP, and biotinylated dUTP.

Oligonucleotide derivatives are also available as labels. For example, etheno-dA and etheno-A are known fluorescent adenine nucleotides which can be incorporated into a reporter. Similarly, etheno-dC is another analog that can be used in reporter synthesis. The reporters containing such nucleotide derivatives can be hydrolyzed to release much more strongly fluorescent mononucleotides by the polymerase's 5' to 3' nuclease activity as nucleic acid polymerase extends a primer during PCR.

Introducing the I-Switch Into Cells

In some embodiments, the sample in which pH is to be measured can be a biological sample, e.g., a biological tissue or a cell or an organism. The method is suitable for measuring pH in a specific region of the cell, e.g., the cytosol, or an organellar space such as, but not limited to, the inner mitochondrial matrix, the lumen of the Golgi, the endoplasmic reticulum, the chloroplast lumen, the lumen of a lysosome, the nucleus, or the lumen of an endosome.

The I-switch can be readily introduced into a host cell, e.g., mammalian (optionally human), bacterial, parasite, yeast or insect cell by any method in the art. For example, I-switch can be transferred into a host cell by physical, chemical or biological means. It is readily understood that the introduction of the oligonucleotides yields a cell in which the intracellular pH may be monitored. Thus, the method can be used to measure intracellular pH in cells cultured in vitro. The I-switch can also be readily introduced into a whole organism to measure the pH in a cell or tissue in vivo. For example, I-switch can be transferred into an organism by physical, chemical or biological means, e.g., direct injection.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York, 2001), and in Ausubel et al. (Current Protocols in Molecular Biology, John Wiley & Sons, New York, 1997).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the I-switch into host cells (in vitro, ex vivo or in vivo). In a specific embodiment, the I-switch may be associated with a lipid. The I-switch associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/I-switch compositions are not limited to any particular structure in solution. For example, they may be present in a bilayer structure, as micelles, or with a "collapsed" structure. They may also simply be interspersed in a solution, possibly forming aggregates which are not uniform in either size or shape.

Liposome-mediated oligonucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments, the lipid may be associated with a hemagglutinating virus (HVJ). This has been shown to facilitate fusion with the cell membrane and promote cell entry of liposome-encapsulated DNA. In other embodiments, the lipid may be complexed or employed in conjunction with nuclear non-histone chromosomal proteins (HMG-1). In yet further embodiments, the lipid may be complexed or employed in conjunction with both HVJ and HMG-1.

In some embodiments, the one or more I-switches are linked to a targeting sequence that directs the I-switch to a desired cellular compartment. Examples of targeting sequences include, but are not limited to, the amino terminal 81 amino acids of human type II membrane-anchored protein galactosyltransferase for directing the fluorescent indicator protein to the Golgi and the amino terminal 12 amino acids of the presequence of subunit IV of cytochrome c oxidase for directing a fluorescent pH indicator protein to the mitochondrial matrix. The 12 amino acids of the presequence of subunit IV of cytochrome c oxidase may be linked to the pH fluorescent indicator protein through a linker sequence.

In Vivo/Ex Vivo Detection of pH in Cells or Tissues Using the I-Switch

In some embodiments, the methods provide for determining the pH of a sample by contacting the sample with an indicator including one or more I-switches whose emission intensity changes as pH varies between pH 4 and 10 or between pH 5 and 7, and exciting the indicator, and then determining the intensity of light emitted by the one or more I-switches at a one or more wavelengths. The emission intensity or signal magnitude of one or more I-switches indicates the pH of the sample. In an illustrative embodiment, the one or more I-switches can be a combination of oligonucleotides similar to the one shown in FIG. 5.

In illustrative embodiments, the I-switch may be used to monitor the pH changes in real-time during cellular processes. In one embodiment, the I-switch is used to monitor endocytosis. While not wishing to be limited by theory, acidification plays a major role in facilitating cargo dissociation from receptors or in mediating cellular entry of toxins and viruses during endocytosis. As demonstrated in the Examples, the I-switch exhibits a pH response inside cells illustrated by the capture of spatiotemporal pH changes associated with endocytosis in living cells.

Fluorescence in the sample can be measured in a variety of ways, such as using a fluorometer or fluorescence microscopy. In general, excitation radiation, from an excitation source having a first wavelength, passes through excitation optics. The excitation optics cause the excitation radiation to excite the sample. In response, labels associated with the one or more I-switches in the sample emit radiation which has a wavelength that is different from the excitation wavelength. Collection optics then collect the emission from the sample. The device can include a temperature controller to maintain the sample at a specific temperature while it is being scanned. If desired, a multi-axis translation stage can be used to move a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In one embodiment, the detecting includes measuring the magnitude of the signal generated, wherein the magnitude indicates the pH of the cell or region thereof. In one embodiment, wherein the magnitude of the signal changes as the pH varies from pH 5 to 10 or pH 5 to 7. For FRET, the emission from the acceptor fluorophore increases as the I-switch forms a closed state, i.e., as the i-motif is formed when the pH decreases. Likewise, the emission from the acceptor fluorophore decreases as the I-switch assumes an open state, i.e., as the i-motif dissociates when the pH increases. For fluorescence quenching, the emission from the fluorophore decreases as the I-switch forms a closed state, i.e., as the i-motif is formed when the pH decreases. Likewise, the emission from the fluorophore increases as the I-switch forms an open state, i.e., as the i-motif dissociates when the pH increases.

As used herein, an "increase" (or "decrease") in a signal from the I-switch refers to the change in a signal in the sample compared to a reference sample. The reference sample may be a control sample (e.g., an untreated population of cells where the effects of a drug or agent are being exampled), or it may be the same sample at a different period of time, for instance, where the intracellular pH is being monitored to follow one or more cellular processes.

As used herein, the term "detectable" refers to a property of the I-switch that allows one to determine the pH of a biological sample by detecting activity, e.g., fluorescence activity, possessed by the I-switch under certain pH conditions. In some embodiments, the signal from the I-switch is normalized by plotting the donor/acceptor (D/A) signal ratio as a function of pH in a standard reference sample. pH variation on a doubly-labeled I-switch changes the ratio between its closed and open states thereby resulting in different ratios of the donor and acceptor intensities (D/A) because of FRET in the closed state due to i-motif formation.

In one embodiment, a pH calibration curve may be generated to which test samples may be compared and normalized. An intracellular calibration curve may be generated as described in the Examples. Briefly, cells are pulsed, washed, incubated with an ionophore in buffers at a given pH and then mildly fixed. Donor and acceptor FRET images are acquired from which D/A ratios are obtained. The mean D/A of individual cells or regions thereof at each pH are plotted as a function of pH for the intracellular pH calibration curve. The D/A ratio of the test sample can be compared to the calibration curve.

In one embodiment, intracellular pH may be monitored for the purposes of examining cellular phenomena and/or screening the effects of various compounds, wherein the level of the signal from an I-switch (e.g., increased or decreased signal) in a test sample at a first time point is determined and compared with the level found in a test sample obtained at a later time point. The change in signal may reflect a relative change in pH between the two samples. For example, where a FRET pair is used as a label, an increase in signal from one time point to another may indicate an increase in pH between the two time points. Likewise, a decrease in signal from one point to another may indicate a decrease in pH. The absolute level of signal may be compared to a reference sample of known standards or reference samples in order to determine the precise pH of the sample. The sample can be classified or assigned to a particular pH value based on how similar the measured levels were compared to the control levels for a given group.

As one of skill in the art will understand, there will be a certain degree of uncertainty involved in making this determination. Therefore, the standard deviations of the control group levels can be used to make a probabilistic determination and the method of this disclosure are applicable over a wide range of probability-based determinations. Thus, for example, and not by way of limitation, in one embodiment, if the measured level of signal falls within 2.5 standard deviations of the mean of any of the control groups, then that sample may be assigned to that group. In another embodiment if the measured level of signal falls within 2.0 standard deviations of the mean of any of the control groups then that sample may be assigned to that group. In still another embodiment, if the measured level of signal falls within 1.5 standard deviations of the mean of any of the control groups then that sample may be assigned to that group. In yet another embodiment, if the measured level of signal is 1.0 or less standard deviations of the mean of any of the control groups levels then that sample may be assigned to that group. Thus, this process allows determination, with various degrees of probability, in which group a specific sample should be placed.

Statistical methods can also be used to set thresholds for determining when the signal intensity in a test sample can be considered to be different than or similar to the reference level. In addition, statistics can be used to determine the validity of the difference or similarity observed between a test sample's signal intensity and the reference level. Useful statistical analysis methods are described in L. D. Fisher & G. vanBelle, *Biostatistics: A Methodology for the Health Sciences* (Wiley-Interscience, NY, 1993). For instance, confidence ("p") values can be calculated using an unpaired 2-tailed t test, with a difference between groups deemed significant if the p value is less than or equal to 0.05.

The I-switch pH sensors have may vary in their respective $pK_a$, and the differences in $pK_a$ can be used to select the most suitable I-switch sensor for a particular application. In general, a sensor should be used whose $pK_a$ is close to the pH of the sample to be measured. For example, the $pK_a$ may be within 1.5 pH unit, within 1.0 pH unit, or within 0.5 pH units of the sample. The $pK_a$ of the I-switch may be changed by, e.g., adjusting the number of cytosine residues in the I-motif or introducing chemical derivatives of cytosine, such as 5-methylcytosine.

To minimize artefactually low fluorescence measurements that occur due to cell movement or focusing, the fluorescence of the I-switch can be compared to the fluorescence of a second sensor, e.g., a second I-switch that is also present in the measured sample. The second I-switch should have an emission spectra distinct from the first I-switch so that the emission spectra of the two sensors can be distinguished. Because experimental conditions such as focusing and cell movement will affect fluorescence of the second sensor as well as the first sensor, comparing the relative fluorescence of the two sensors may allow for the normalization of fluorescence. A convenient method of comparing the samples is to compute the ratio of the fluorescence of the first fluorescent protein pH sensor to that of the second fluorescent protein pH sensor.

In one embodiment, circular dichroism spectroscopy may be used to detect changes in the secondary structure of the I-switch in response to changes in pH. Circular Dichroism (CD) is observed when optically active matter absorbs left and right hand circular polarized light slightly differently. It is measured with a CD spectropolarimeter. In another embodiment, change in intracellular pH may be detected by observing Raman band changes in the I-switch. In this embodiment, the I-switch contains a gold nanoparticle label and a Raman tag. The Raman band changes may be detected when the gold nanoparticle is brought close to a Raman tag.

Kits

The materials and components described for use in the methods may be suited for the preparation of a kit. Thus, the disclosure provides a detection kit useful for determining the pH of a cell or region thereof. Specifically, the technology encompasses kits for measuring the pH of one or more cells in a sample. For example, the kit can comprise a labeled I-switch capable of detecting the pH of a cell or region thereof.

In one embodiment, the methods described herein may be performed by utilizing pre-packaged diagnostic kits comprising the necessary reagents to perform any of the methods of the technology. For example, such a kit would include a detection reagent for measuring the pH of a cell or region thereof. In one embodiment of such a kit, the detection reagents are an I-switch, such as that shown in FIG. 5 and defined by the sequences in Table 1. Oligonucleotides are easily synthesized and are stable in various formulations for long periods of time, particularly when lyophilized or otherwise dried to a powder form. In this form, they are easily reconstituted for use by those of skill in the art. Other reagents and consumables required for using the kit could be easily identified and procured by those of skill in the art who wish to use the kit. The kits can also include buffers useful in the methods of the technology. The kits may contain instructions for the use of the reagents and interpreting the results.

In another embodiment, the technology provides a kit comprising at least one sample (e.g., a pH standard) packaged in one or more vials for use as a control. Each component of the kit can be enclosed within an individual container and all of the various containers can be within a single package, along with instructions for interpreting the results of the assays performed using the kit.

EXAMPLES

The present methods and kits, thus generally described, will be understood more readily by reference to the following examples, which are provided by way of illustration and are not intended to be limiting of the present methods and kits. The following is a description of the materials and experimental procedures used in the Examples.

Materials.

HPLC purified DNA oligonucleotides were used without further purification whereas fluorescently modified oligonucleotides were ethanol precipitated prior to further use. Nigericin, biotin labeled human holo-Transferrin and Streptavidin were obtained from Sigma. FITC labeled dextran, LYSO TRACKER™ red, MITO TRACKER® Green were obtained from Molecular Probes, Invitrogen. All other reagents were purchased from Sigma-Aldrich unless otherwise specified.

Sample Preparation.

Stock DNA solutions were prepared by dissolving lyophilized DNA in Milli-Q water and stored at −20° C. until further use. Five micromolar (5 µM) of O1, O2 and O3 were mixed in equimolar ratios in 20 mM potassium phosphate buffer of desired pH containing 100 mM KCl. The resultant solution was heated to 90° C. for 5 min, cooled to the room temperature over 3 hr at 5° C./15 min and equilibrated at 4° C. overnight. Prior to the experiment, the solution was diluted to 80 nM in appropriate buffer containing 100 mM KCl unless otherwise mentioned.

Circular Dichroism Spectroscopy.

All CD scans were performed on a JASCO J-815 spectrophotometer equipped with a temperature controller. A 5 µM stock of the I-switch was annealed. Samples at pH 5 and 7.3 were prepared at 20 mM potassium phosphate in 100 mM KCl as stated earlier. Samples were then diluted to 1 µM in the appropriate buffer and equilibrated for an hour and are presented as an average of 5 successive scans.

Steady State Fluorescence Measurements.

All fluorescence spectra were measured on a Jasco-815 CD spectrometer with an inbuilt fluorimeter. Fluorescently labeled I-switch containing O1 labeled with ALEXA FLUOR™ Alexa/188 (O1-488) and O2 labeled with ALEXA FLUOR™ 647 (O2-647) were prepared as stock solution of 5 µM stock in 20 mM pH 5.5 potassium phosphate, 100 mM KCl. Samples were diluted to 80 nM in appropriate buffer for all fluorescence experiments. The samples were excited at 488 nm and emission collected between 505 nm-750 nm. FRET efficiencies were calculated using the formula, $E=1-I_{DA}/I_D=1/[1+(R/R_o)^6]$, where $I_D$ is the intensity of the donor in the absence of the acceptor, $I_{DA}$ is the intensity of the donor in the presence of the acceptor, $R_o$ is the Förster's distance and R is the interfluorophore distance. $R_o$ for ALEXA FLUOR™ 488 and ALEXA FLUOR™ 647 was taken as 50 Å.

FRET Pair Used in the Study.

Three different FRET pairs were used in this study. ALEXA FLUOR™ 546 ALEXA FLUOR™ 647 was used to characterize the closing and opening of I-switch by pH cycling as well as to confirm the conformation of the closed state. BODIPY® TMR-ALEXA FLUOR™ 647 was used in the following cases (i) a distinct FRET pair to confirm that the pH profile of the I-switch is not due to dye sensitivity, but due to i-motif formation (ii) colocalization studies of I-switch with FITC dextran, (iii) colocalization studies of I-switch in Rab 5-GFP expressing hemocytes and (iv) to prove integrity of the I-switch scaffold under the conditions used. For all other studies, ALEXA FLUOR™ 488-ALEXA FLUOR™ 647 labeled I-switch was used.

pH Cycling.

pH cycling experiments were performed on a Fluorolog-Spex spectrophotometer. I-switch (5 nM) was cycled between pH 5 to pH by the alternate addition of 3 µL of 0.5 N HCl and 4 µL of 0.5 N KOH, respectively.

Time Resolved Fluorescence Measurement.

Time resolved experiments were measured in Zeiss LSM 5 Meta multiphoton set up. Briefly, fluorophores excited by multiphoton excitation were built on a Zeiss LSM 510 Meta microscope (Carl Zeiss) with 63×1.4 numerical aperture (NA) objective coupled to the femtosecond-pulsed Tsunami Titanium:Sapphire tunable pulsed laser. Fluorescence was collected in Hamamatsu R3809U multi-channel plate photomultiplier tubes (PMTs; Hamamatsu Photonics) while TCSPC was accomplished using a Becker & Hickl 830 card (Becker and Hickl). For multiphoton excitation of ALEXA FLUOR™ 488, 720 nm excitation wavelength was used. The repetition rate of the pulsed laser is 80.09 MHz (12 ns). The instrument response function (IRF) was calculated from 10-16-nm gold particles dried on a coverslip as a second harmonic generator; full width at half maximum (FWHM) of IRF is approximately 60 ps. Experimentally measured fluorescence decay is a convolution of the IRF with the intensity decay function. Average lifetimes at different pH were obtained from the intensity decay data were fit to the appropriate equations by an iterative reconvolution procedure using a Levenberg-Marquardt minimization algorithm.

Cell Culture and Labelling.

Hemocytes were obtained from wandering third instar Drosophila larvae. Briefly, larvae were surface sterilized and then punctured to release the hemolymph into complete insect medium that is composed of Schneider's insect medium supplemented with 10% non-heat inactivated FBS, 1 µg/ml bovine pancreatic insulin, 150 µg/ml penicillin, 250 µg/ml streptomycin, 750 µg/ml glutamine. The medium is then plated onto 35 mm coverslip dishes. Labeling of cells with fluorophores was performed 1.5 hours after dissection.

For pH measurement experiments, cells were imaged live, after chasing the probes for the stated time points. The pH standard curve was generated in cells by briefly fixing cells (for 1 min) with 2.5% paraformaldehyde (PF) and then adding the ionophore, nigericin along with medium 1 buffered to appropriate pH (ranging from 5-7). For colocalization experiments cells were fixed with 2.5% Pf for 20 minutes. For colocalization of Rab5 with the sensor, transgenic flies expressing Rab5GFP were crossed to flies expressing Heme-Gal4 and GFP positive progeny were used for hemocyte cell culture. Stable line of Drosophila SR+ cells expressing the human Transferrin receptor were used for labeling experiments. Cells were labeled on ice with the switch conjugated to biotinylated Transferrin (Sigma), and then pulsed at room temperature for 15 min. Cells were then moved to ice and the treated with low pH ascorbate buffer to remove the remaining receptor-bound ligands. The Transferrin conjugated with the I-switch was imaged after fixation with 2.5% formaldehyde.

Fluorescence Microscopy and Image Analysis.

All the wide-field images were collected using a Nikon inverted microscope equipped with 60×, 1.4 NA objectives, a mercury arc illuminator (Nikon, Japan), and a cooled CCD camera (Andor, USA) controlled by Metamorph software (Universal Imaging, PA). Three sets of images were taken corresponding to (I) image at donor emission wavelength upon donor excitation (donor image), (II) image at acceptor emission wavelength (acceptor FRET) upon donor excitation and (III) image at acceptor emission wavelength (Acceptor image) acceptor excitation. Confocal imaging was carried out on an Olympus Fluoview 1000 confocal microscope (Olympus, Japan) using an Argon ion laser for 488 nm excitation and He—Ne laser for 543 excitation with a set dichroics, excitation, and emission filters suitable for each fluorophore. Cross talk and bleed-through were measured with donor only and acceptor only species and found to be negligible for ALEXA FLUOR™ 488/647 pair. Autofluorescence was measured on unlabeled cells. All the images were then background subtracted taking mean intensity over a large cell free area. Donor and acceptor images were colocalized and endosomes showing good colocalization were analyzed using ImageJ and total intensity as well as mean intensity in each endosome was measured in donor and acceptor channels. A ratio of donor to acceptor intensities (D/A) was obtained from. Five independent measurements were presented as the mean±standard error (s.e.m).

Ratiometric pH Measurements.

The in vitro pH calibration profile was obtained on A JASCO-815 CD spectrometer. I-switch at 80 nM was prepared in buffers of different pH values from 4 to 7.3. Measurements from two independent samples were taken at given pH and the mean donor intensity (D) at 520 nm and mean acceptor intensity (A) at 665 nm were recorded. D/A values at each pH were plotted as a function of pH to give the in vitro calibration curve. Error bars were representative of the standard error between five independent measurements. For the intracellular pH calibration curve, cells were pulsed, chased for 5 min, washed, incubated with 10 µM Nigericin in buffers at a given pH and then mildly fixed. Donor and acceptor FRET images were acquired as described earlier from which D/A ratios were obtained. The mean D/A of individual endosomes with associated s.e.m at each pH were plotted as a function of pH for the intracellular pH calibration curve. Spatiotemporal pH changes were followed by comparing the spread in D/A values of ~80 endosomes for 5 independent experiments at the specified chase time to the calibration curve.

Real-time pH measurement data was generated by imaging different portions on a single coverslip over 2 h with a time interval of 5 minutes each, such that each time frame has five images covering five different places in the coverslip. From those five fields of view, 40 endosomes at each time point were quantified and mean D/A (for two independent experiment)±s.e.m was calculated and plotted over time.

Protein Conjugation of I-Switch.

For conjugation to transferrin, I-switch incorporated with a biotin label was used. O1-488 and O2-647 was hybridized with 5'-Biotinylated O3 in pH 5.5 phosphate buffer. 5 µL of 5 µM biotinylated switch ($I_B$) was diluted 2 fold with PBS pH 7.4 and to it 5 µL of Streptavidin (1 mg/ml) was added slowly and incubated at room temperature for 1 hr. Conjugation ($I_{B-SA}$) was confirmed by agarose gel electrophoresis (3%). This conjugate ($I_{B-SA}$) was further conjugated with biotinylated holo-Transferrin ($Tf_B$) similarly in a 1:2 ratio. Excess Biocytin (1 nanomole) was added after 1 h to the solution to prevent aggregation. Formation of Transferrin conjugated I-switch ($I_{B-SA}$-$Tf_B$) was confirmed by gel electrophoresis. The presence of Transferrin with the sensor was confirmed by colocalization experiments and by competing out the sensor with ALEXA FLUOR™ 568 labeled as well as unlabeled Transferrin.

Example 1

Construction and Characterization of I-Switch pH Sensors

Design and Working Principle of the I-Switch.

The I-switch is composed of three sequences, O1, O2 and O3. O1 and O2 are partially complementary to O3 to form a linear duplex leaving a base gap which acts as a fulcrum to facilitate closing and opening of the construct. as shown in FIG. 1a. O1 and O2 have single stranded C-rich overhangs (FIG. 5) designed such that each overhang forms one half of a bimolecular i-motif. At acidic pH, these overhangs are protonated and the assembly can fold to form an intramolecular i-motif (FIG. 1a). For fluorescence measurements, O1 and O2 are modified with different fluorophores. O1 was labeled with ALEXA FLUOR™ 488, ALEXA FLUOR™ 546 or BODIPY® TMR with a C7 linker and O2 was attached similarly to ALEXA FLUOR™ 647. For conjugation studies, O3 was modified with biotin at 5' terminus with a C6 linker.

CD Studies to Prove Open and Closed Conformations.

Figure 6:
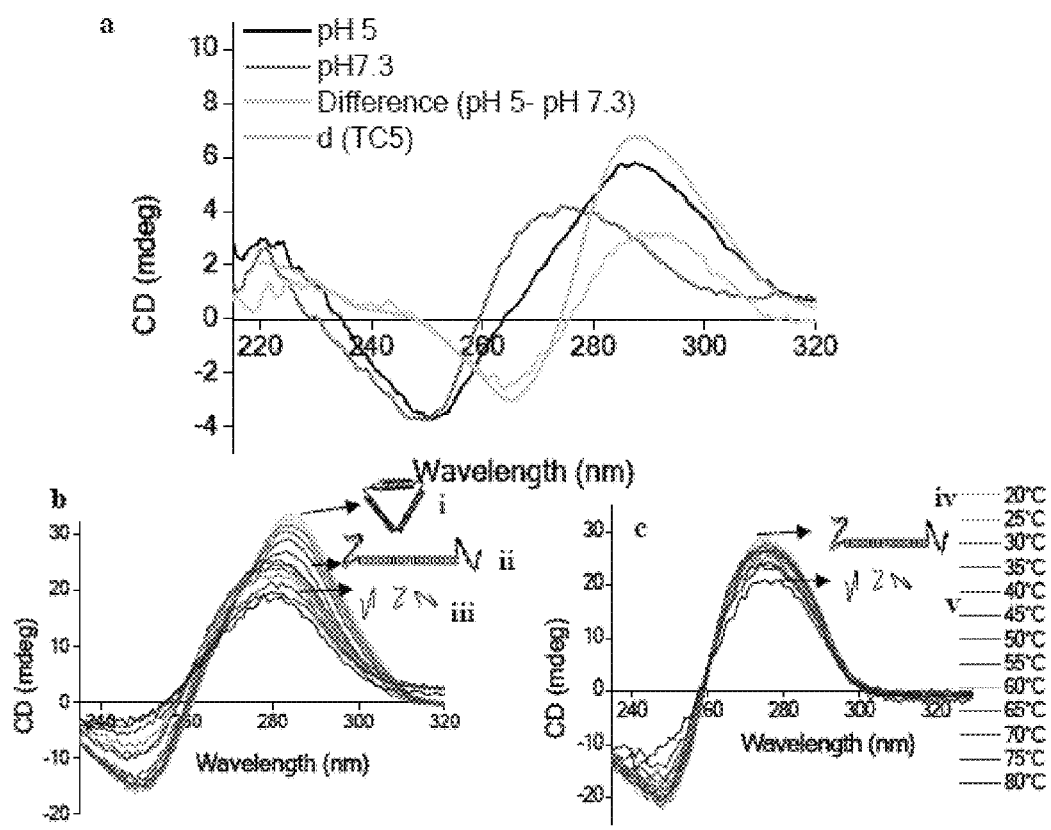
FIG. 6a is a graph of CD spectra of the I-switch at pH 7.3, pH 5 and difference spectra (pH 5-pH 7.3.)
FIGS. 6b and 6c are graphs of CD spectra which demonstrate i-motif formation.

CD spectroscopy on the I-switch showed that this assembly adopts an extended conformation at pH 7.3 while at pH 5 the single stranded overhangs form an i-motif, yielding a 'closed state' (FIG. 6). The I-switch shows a positive peak at 278 nm and a negative peak at 248 nm which resembles a B-DNA duplex, whereas spectra taken at pH 5 showed a shift in circular dichroism (CD) spectra with positive and negative peaks at 285 nm and 251 nm respectively (FIG. 6a). The difference spectra between the conformations of the ternary complex at pH 5.0 and pH 7.3 showed a positive peak at 288 nm with a negative peak centered at 262 nm which is in perfect agreement with the characteristic peaks for $DNA_4$ i-motifs. When this difference spectrum was compared with a well characterised i-motif [d(TC5)]$_4$, it perfectly recapitulated the peak pattern characteristics of i-motif. This indicates that at pH 5.0, the ternary assembly of O1, O2 and O3 is composed of duplexed regions as well as an i-motif.

In order to confirm this, a thermal melt of the complex at pH 5 was followed by CD (FIG. 6b). One (1) µM of I-switch in 20 mM potassium acetate buffer, 100 mM KCl at pH 5 was scanned from 20-80° C. in steps of 5° C. The spectra were recorded between 330 and 235 nm as an average of 8 successive scans. At pH 5, two isochroic points were observed (FIG. 6b), indicating that there were two transitions (one at 50° C. and the other at 65° C.). At 50° C., the CD signature showed abolition of the i-motif component in the structure, leaving only a signature corresponding to a duplex. At 65° C., this duplex structure too was lost yielding a signature corresponding to single stranded DNA (iii). The difference spectrum between the traces at 25° C. and 50° C. showed a trace resembling $DNA_4$ i-motifs, confirming that it was indeed the i-motif component that was melted by ~50° C. In contrast, the CD melting experiments done with 1 µM of construct at pH 7.3 (FIG. 6c), showed only one isochroic point corresponding to the melting transition of the duplex (iv) to a single stranded state (v).

FRET and Distance Measurements.

Figure 7:
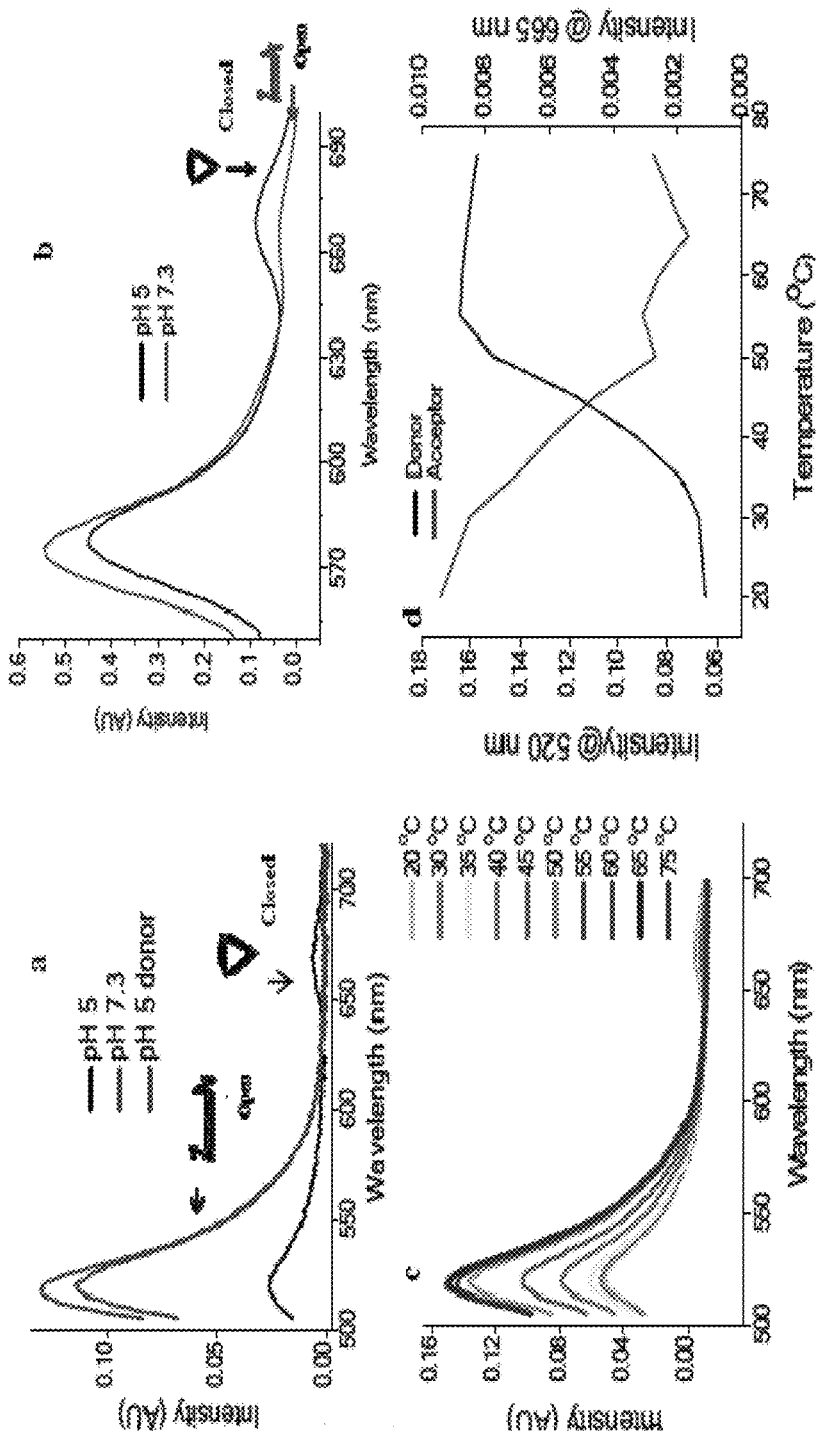
FIG. 7 is a series of graphs of FRET to demonstrate closed and open states.

FRET measurements were carried out on I-switch composed of labeled DNA strands with ALEXA FLUOR™ 488 as a donor and ALEXA FLUOR™ 647 as acceptor. This FRET pair has a Förster distance of 5.0 nm. Fluorescence spectra were taken at pH 5 and pH 7.3 in phosphate buffer having 100 mM KCl. 54-60% quenching was observed from the closed state to open state giving an interfluorophore distance of 4.6±0.5 nm, which is in good agreement from a coarse grained model taking NMR parameters from d(CCCCAA) i-motif (FIG. 7). In order to ensure that the observed FRET was fluorophore independent, another FRET pair was chosen by labeling O1 with BODIPY® TMR and O2 with ALEXA FLUOR™ 647, which also showed similar energy transfer. When the I-switch incorporated fluorescent labels at a different location, i.e., 5' and 3' termini of O3 with ALEXA FLUOR™ 546 and ALEXA FLUOR™ 647, we observed FRET that incorporated the thickness of the duplex arms as well that led to a distance of 7.8±0.5 nm (theoretically predicted distance 7.3 nm). This confirms that in the closed state, the I-switch comprise two duplex arms that are united via their C-rich single stranded overhangs by forming an intramolecular i-motif.

CD melts revealed a lower melting species at 45-50° C. To confirm that this is due to the melting of an intramolecular i-motif, fluorescence melts were carried out with the sample in which both the overhangs were labeled with dyes. In the closed state via intramolecular i-motif formation, the two dyes come into close proximity (4.6 nm) leading to high FRET. As a function of increasing temperature, thermal denaturation of the i-motif should abolish FRET and therefore donor intensity of the I-switch should increase with a concomitant decrease in acceptor intensity. FIG. 7 shows the expected sigmoidal increase in donor and concomitant decrease in acceptor fluorescence with a melting temperature of 45° C. consistent with CD data and confirming intramolecular i-motif formation.

Figure 8:
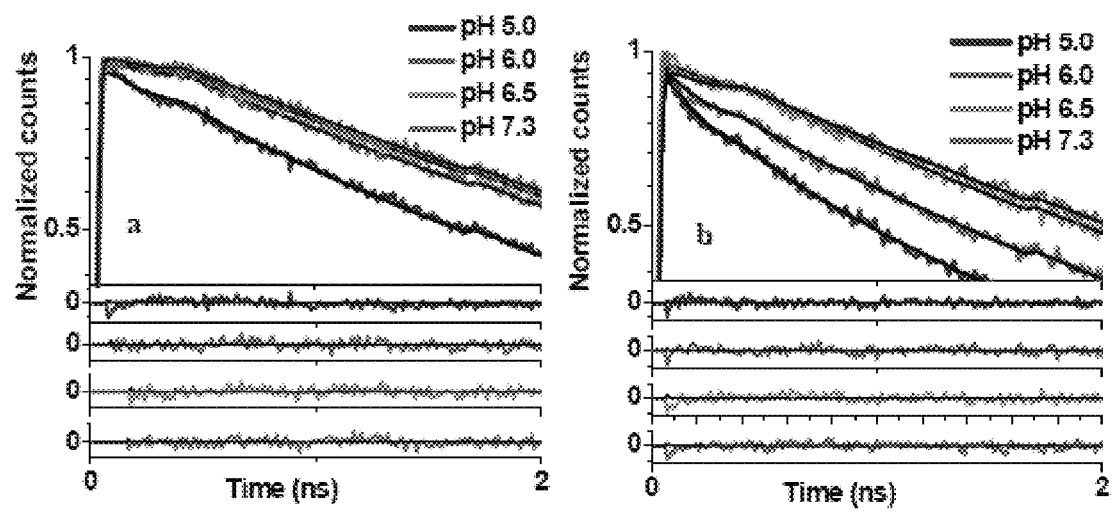
FIG. 8 shows graphs of time resolved fluorescence spectra of differently labeled I-switch assemblies at different pH.

FRET was further confirmed through time resolved fluorescence measurements (FIG. 1d inset) of the donor in the closed and open states. At pH 7.3, donor lifetimes of ALEXA FLUOR™ 488 labeled I-switch showed only a marginal difference in the donor-only labeled I-switch (~3.77 ns) and the doubly (ALEXA FLUOR™ 488-ALEXA FLUOR™ 647) labeled complex (~3.50 ns). However, at pH 5, the donor lifetime showed a significant change to 2.1 ns for the doubly labeled I-switch, while the donor-only I-switch showed a meagre decrease (~3.02 ns) (FIG. 8). In order to see if the I-switch could switch reversibly between the 'closed' and 'open' states upon pH variation, 5 nM of doubly labeled I-switch (ALEXA FLUOR™ 546/647-FRET pair) in 100 mM KCl was subjected to pH cycling alternately between pH 5 and 8 by adding acid or base to the solution (FIG. 1b). Donor fluorescence at 570 nm was followed with time. At high pH, donor fluorescence of the open state was high. At pH 5, this decreased as a result of FRET due to closed state formation as expected. Switching is highly reversible over at least 20 cycles with negligible change in efficiency. The response times of the I-switch, are fairly fast ($T_{1/2\ closing}$~75 s, $T_{1/2 opening}$~3 s, FIG. 1c).

Fluorescence Lifetime Experiments Confirms FRET.

Donor fluorescence intensity decays for donor-only (D) labeled (Alexa-488) and donor-acceptor (DA) labeled (ALEXA FLUOR™ 488-as donor and ALEXA FLUOR™ 647 as acceptor) construct were obtained from TCSPC experimental setup. To quantify donor fluorescent lifetime, intensity decays were fitted to a bi-exponential decay model $I=I_o[A_1 e^{(-t/\tau_1)} + A_2 e^{(-t/\tau_2)}]$ by an iterative reconvolution procedure using a Levenberg-Marquardt minimization algorithm, where $I_0$ is initial fluorescence intensity; $A_1$, $A_2$ are the normalized amplitude of individual components; and $\tau_1, \tau_2$ are the lifetimes of each components. Fluorescence decays were considered well fit when three criteria were met: a) reduced $\chi^2$ was less than 1.2, b) residuals were evenly distributed across the full extent of the data, and c) visual inspection ensured that the fit accurately described the decay profile. A representative time resolved fluorescence intensity decay and fit from donor-only sample is shown in FIG. 8a. Parameters such as amplitude ($A_1$, $A_2$) and decay time constants ($\tau_1$, $\tau_2$) were obtained after satisfying above criteria of fitting and the average lifetime was calculated using the formula:

$$\tau_{av} = \frac{(A_1 \times \tau_1) + (A_2 \times \tau_2)}{A_1 + A_2}$$

(Where $A_1+A_2$ was normalized to 1) and listed in the table below. Although, at pH 7.3 D-labeled construct showed an average lifetime of 3.77 ns which marginally decreased to 3.5 ns at pH 6, at pH 5 it dropped to 3.0 ns that can be explained by donor quenching due to i-motif formation. In contrast, at both pH (6 and 5) donor lifetime exhibited dramatic decrease in DA-labeled (2.7 ns and 2.1 ns) sample compared to D-labeled (3.5 ns and 3.5 ns) sample respectively (FIG. 8b). It is also evident that at both pH 6 and 5, a faster decay component appears which can only be fitted with a third exponent. Appearance of this faster component can be explained as a result of FRET. Average lifetime extracted from the all decay curves are summarized in Table 2 and Table 3, which show dual labeled I-switch (ALEXA FLUOR™ 488/647) as well as donor-only controls in vitro and inside endosomes, respectively.

TABLE 2

| pH | Donor Only ($T_d$) (ns) ± SD | Dual Labeled ($T_{da}$) (ns) ± SD |
|---|---|---|
| 5.0 | 3.021 ± 0.003 | 2.182 ± 0.094 |
| 6.0 | 3.584 ± 0.013 | 2.728 ± 0.035 |
| 6.5 | 3.737 ± 0.015 | 3.272 ± 0.012 |
| 7.2 | 3.777 ± 0.027 | 3.506 ± 0.015 |

TABLE 3

| pH | Timepoint inside endosome (min) | Donor Only ($T_d$) (ns) ± SD | Dual Labeled ($T_{da}$) (ns) ± SD |
|---|---|---|---|
| 7 | — | — | 1.173 ± 0.035 |
| 5.5 | 30 | — | — |
| 5 | 120 | 0.8 | 0.735 ± 0.067 | pH Calibration Curve of the I-Switch.

The fluorescence properties of the I-switch as a function of pH were investigated in order to determine its regime of pH sensitivity (FIG. 1d). pH variation on the doubly (ALEXA FLUOR™ 488-ALEXA FLUOR™ 647) labeled I-switch changes the ratio between its closed and open states resulting in different ratios of the donor and acceptor intensities (D/A) due to FRET in the closed state due to i-motif formation. A plot of D/A as a function of pH (FIG. 2a), gave a standard in vitro pH calibration curve for the I-switch that showed a sigmoidal increase from pH 5.0 to 6.8.

Figure 9:
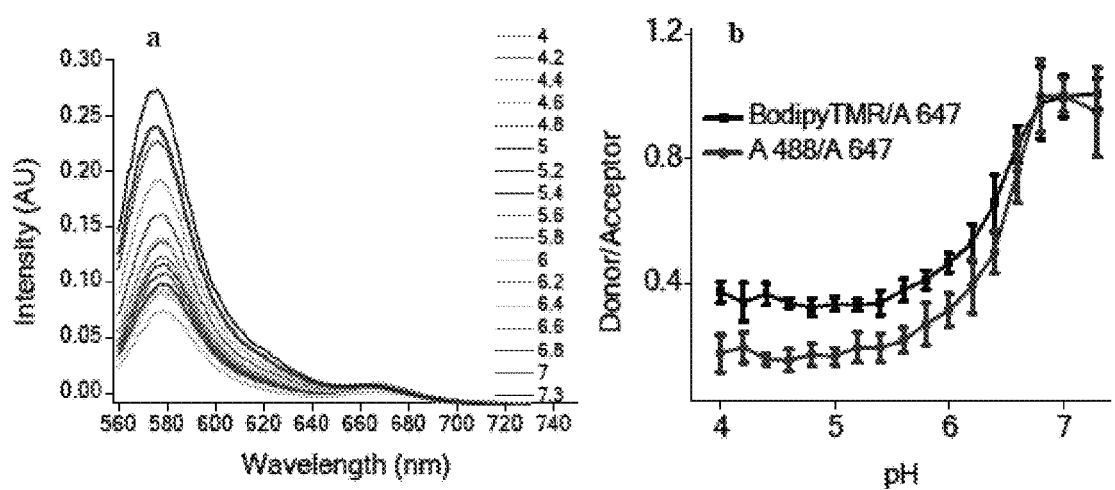
FIG. 9a is a graph of fluorescence intensity plotted as a function of pH to generate standard curve shown in FIG. 9b. Data is represented as a mean of four individual experiments±s.e.m plotted as a function of pH.

This was further confirmed by using another FRET pair, BODIPY® TMR-ALEXA FLUOR™ 647 which showed identical regimes of pH sensitivity (FIG. 9). The I-switch with two different FRET pairs BODIPY® TMR-ALEXA FLUOR™ 647 as shown in FIG. 9a, and comparison with ALEXA FLUOR™ 488/647 FRET pair, which is shown in FIG. 9b, 80 nM I-switch labeled with BODIPY® TMR and ALEXA FLUOR™ 647 was taken in buffers ranging from pH 4 to 7.3 containing 100 mM KCl. BODIPY® TMR was excited at 543 nm and spectra was recorded from 560 to 750 nm. D/A curve as a function of pH was generated from the ratio of donor (579 nm) to acceptor (665 nm) intensities at the given pH values. Fold increase for this FRET pair, calculated as described in main text, was found to be 3.5 while the fold increase in case of ALEXA FLUOR™ 488-ALEXA FLUOR™ 647 pair was found to be 5.5. Due to higher dynamic range, ALEXA FLUOR™ 488/647 was used for further studies unless otherwise specified. Importantly, the regime of pH sensitivity in both cases is identical indicating that the transition is completely fluorophore independent.

This reaffirmed that the pH sensitivity is not due to the fluorophores, but to the pH response of the underlying DNA scaffold, which is also consistent with other unimolecular i-motif switches (Liu et al., *Angew. Chem. Int. Edn.*, 42:5734-5736 (2003); Liedl et al., *Nano Lett.* 5:1894-1898 (2005)). ALEXA FLUOR™ 488/647 labeled I-switch showed a ~5.5 fold increase in vitro revealing unprecedented dynamic range in the pH regime 6 to 7. Thus, the compositions described herein are useful in methods for determining the pH of a cell or region thereof.

Example 2

Use of I-Switch to Measure Endosomal pH

I-Switch and Endocytosis.

Figure 10:
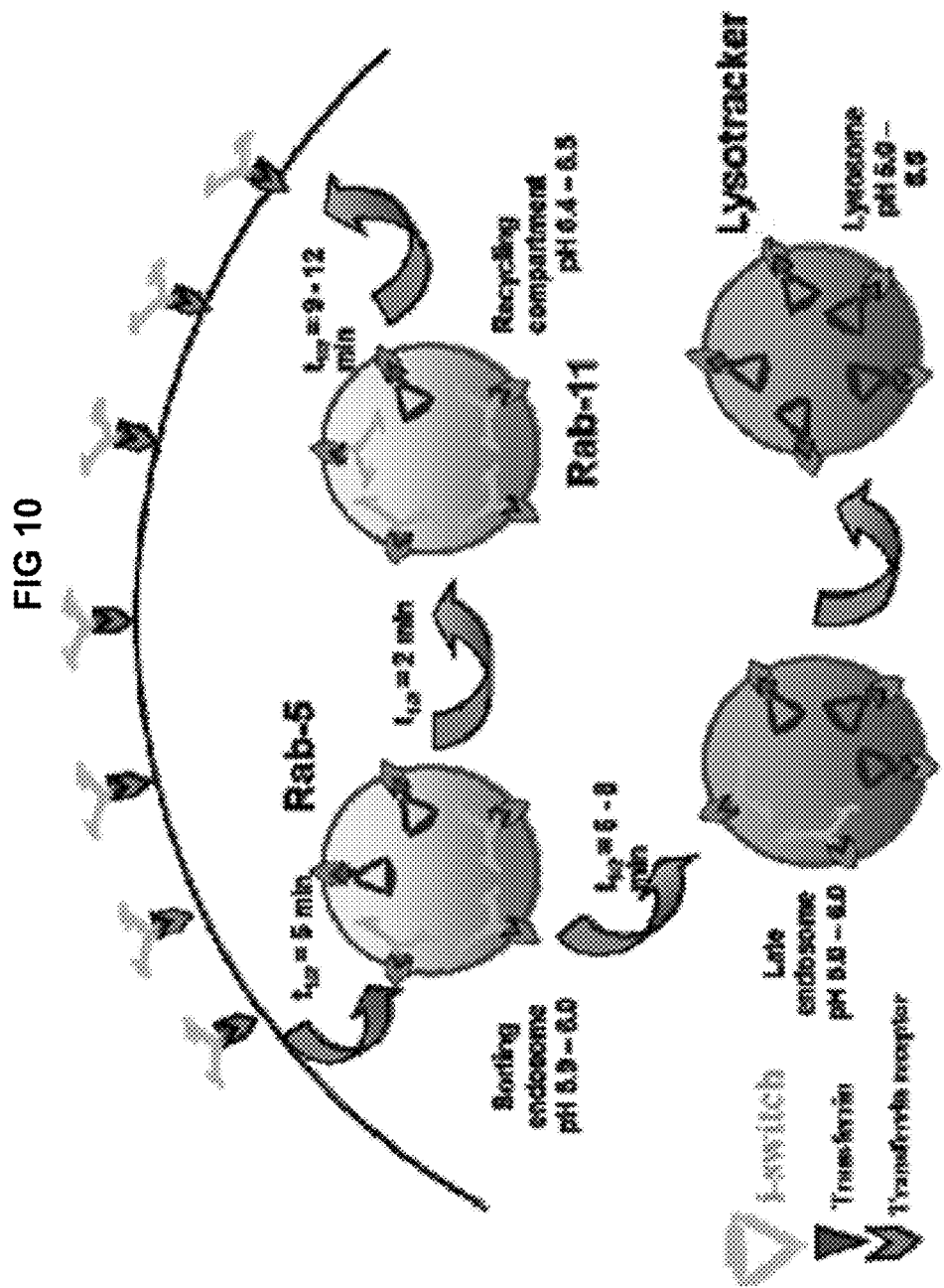
FIG. 10 is a schematic of the internalization of I-switch when tagged with Transferrin. At early time points, early endosomes are Rab-5 positive and relatively less acidic. These progressively mature to lysosomes in about 2 hrs which is much more acidic and stained by LYSO TRACKER®.

Cellular processes such as endocytosis show characteristic acidification profiles that are integral to endosome maturation, vesicle and cargo functions such as sorting of secretory molecules, growth factors, nutrients and toxins (FIG. 10). There are several mechanisms of endocytosis and of specific interest to the I-switch is the receptor mediated endocytotic pathway. When a specific ligand binds with its receptor, the ligand is internalized by the cell through the formation of a vesicle termed as the early endosome. The early endosome has a pH 6 to 6.5. Rab 5 is a GTPase which is localised in early endosomes and is therefore used as a molecular marker for an early endosome. The early endosome gradually matures to late endosome and lysosome which is identified by LysoTracker™ red staining.

Figure 2:
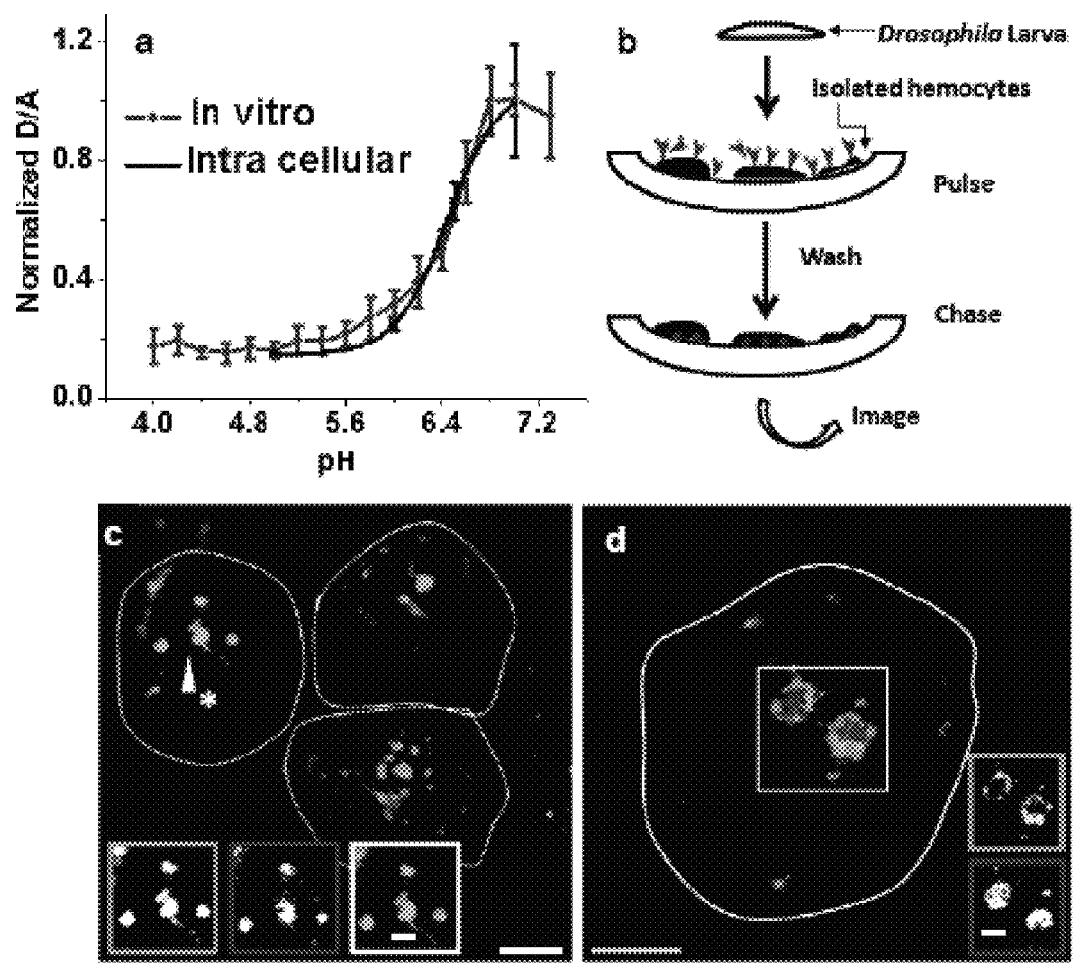
FIG. 2 shows I-switch internalization and function within endosomes of Drosophila hemocytes.

As early endosomes mature to late endosomes and finally to lysosomes, they undergo a characteristic change of pH ranging from 6-6.2 in early endosomes, to pH 5.5 and 5 in the late endosome and lysosome respectively. The capacity of the I-switch to function inside living cells was investigated by detecting endosome maturation in *Drosophila* hemocytes. *Drosophila* hemocytes were 'pulsed' or incubated with a mixture of I-switch labeled with BODIPY® TMR (80 nM) and FITC-Dextran (1 mg/mL), a marker of the endosomal fluid phase. FIG. 2c shows an image of *Drosophila* hemocytes pulsed (5 min) and chased for 5 min, fixed and imaged in a confocal microscope. Importantly, the I-switch was found to be localized in distinct punctate structures ~1 µm in size. When these images were overlayed with co-internalized FITC-Dextran images, these puncta were found to colocalize (~90%), indicating that the I-switch indeed entered endosomes (FIG. 2c).

Integrity of the I-Switch Inside Cells.

Figure 11:
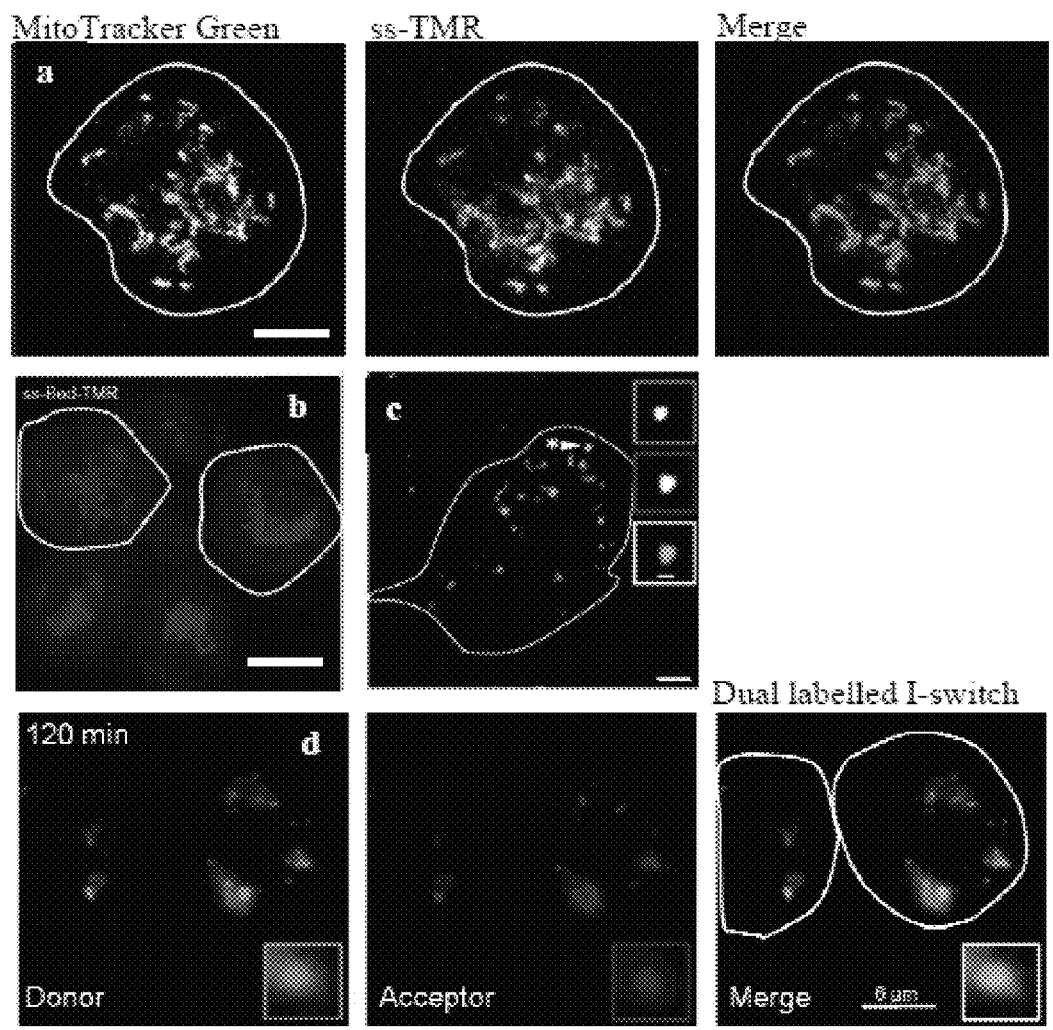
FIG. 11a shows co-localization of MITO TRACKER® Green with ss-TMR in mitochondria.
FIG. 11b is a micrograph showing hemocytes pulsed with O1-BODIPY™ TMR (ss DNA attached to BODIPY® TMR) and chased for 5 min stained tubular compartments corresponding to mitochondria.
FIG. 11c and FIG. 11d show ALEXA FLUOR™ 488/647 labeled and BODIPY® TMR-ALEXA FLUOR™ 647 labeled I-switch pulsed for 5 min, chased for 2 h and imaged. Scale Bar: 6 µm, inset: 1 µm.
Figure 12:
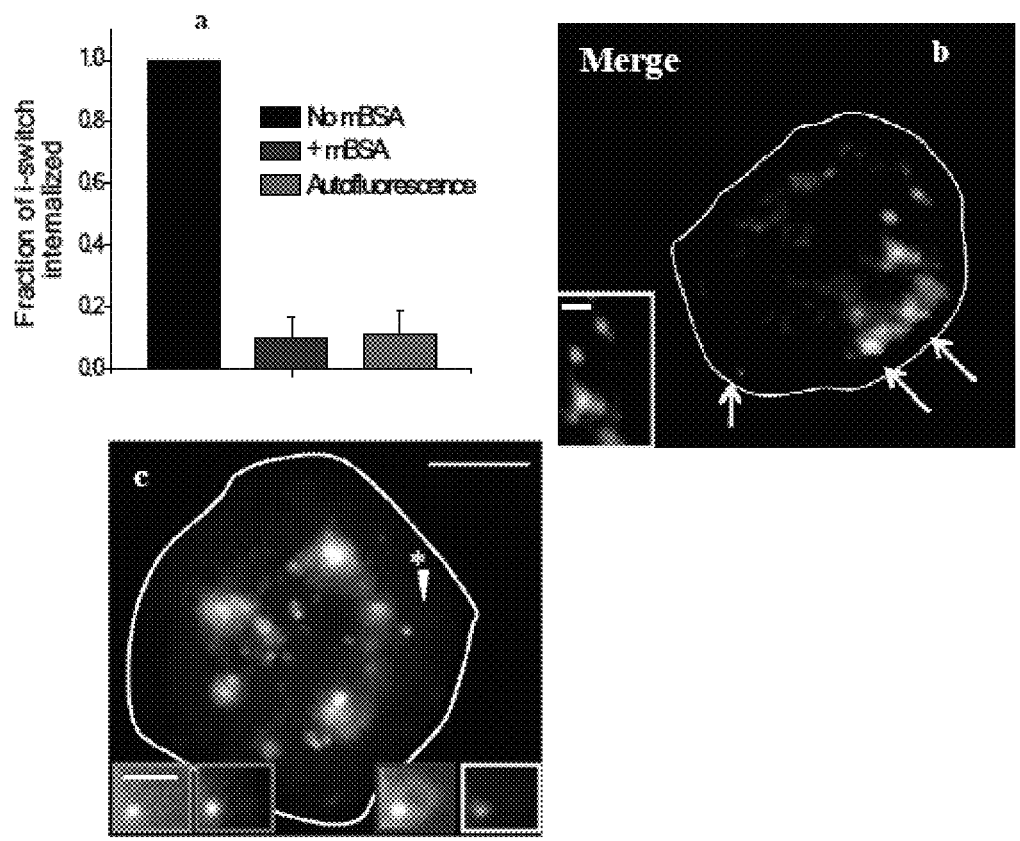
FIG. 12a is a graph showing quantification of I-switch internalization by Drosophila hemocytes in the presence and absence of excess of maleylated BSA (mBSA, 100 µg/ml) that saturates ALB receptors.
FIG. 12b shows co-localization of endocytosed dually labeled I-switch with Rab-5 positive endosomes.
FIG. 12c is a micrograph showing that I-switch accumulates in lysosomes (marked with LYSO TRACKER® Red) at t=2 h. Scale Bar 5 µm, insets b 1 µm and c 3 µm.

Next, in order to check the integrity of the I-switch in living cells over the time period required for endosomal maturation, we followed the I-switch inside endosomes for a period of 5 min, 1 h and 2 h. When cells were incubated with single stranded DNA labeled with TMR (ss-TMR) which is known to be mitochondriotropic, significant fluorescence was seen in cytoplasm clearly marking tubular compartments resembling mitochondria. Colocalization with MITO TRACKER® confirmed that these were indeed mitochondria (FIG. 12a). Also, we observed the following: (I) similarly single stranded DNA labeled with BODIPY® TMR also accumulated in mitochondria (FIG. 12b), (II) when the I-switch is improperly formed (non-annealed mixture of labeled O1, O2 & O3) or a sample of labeled O1 complexed with either only O2 or only O3, instantaneous accumulation of fluorescence is seen in the mitochondria due translocation of Bodipy TMR label out of the endosome. However, when O1-BODIPY® O1 TMR is complexed with both O2 and O3 to form the I-switch, the fit I-switch can no longer translocated out of endosome in the perfectly complexed state, remaining in punctate structures corresponding endosomes (it behaves similar to ALEXA FLUOR™ 488/647 labeled switch in FIG. 11c). This is thus a good indicator of the stability and integrity of the I-switch inside cells. If the I-switch is degraded inside cells, the increase in cytoplasmic fluorescence as well as fluorescence accumulation in mitochondria would be observed. On the timescales investigated (~2 h), the I-switch labeled with BODIPY® TMR, based on the early observable physical property of change in translocation out of the endosome, is stable inside cells. Until the 2 h time point, the I-switch is in punctate endosomal structures indicating that it is stable inside cells on these time scales (FIG. 11d). This was further confirmed by fluorescence lifetime measurements of the donor on doubly-labeled I-switch (Table 2B) inside endosomes. When the lifetime of donor in dual labeled I-switch was measured inside endosomes at t=2 h, these showed characteristic low donor lifetimes (0.8 ns). Upon pH clamping of these endosomes at pH 5, similar donor lifetimes were observed (0.74 ns) indicating that at t=2 h, both fluorophores on the I-switch were within FRETting distance. Upon clamping endosomes at pH 7, when the donor was out of FRETting distance, distinctly higher lifetime of 1.2 ns was observed. These experiments confirm that the I-switch is stable inside cells over these time scales and that the I-switch is useful in methods for determining the pH of cells and regions thereof.

Example 3

Spatio-Temporal pH Mapping of the ALBR Endocytic Pathway

It is known that cargo entering cells via endocytic pathways, such as the anionic ligand binding receptor (ALBR) pathway merge with FITC dextran labeled endosomes at the indicated chase times. Competition experiments with maleylated BSA (mBSA) that is known to adopt the ALBR mediated endocytic route in hemocytes indicated that the I-switch exclusively marks out endosomes along this pathway. Cells were pulsed with a mixture of I-switch (ALEXA FLUOR™ 647) (80 nM) and mBSA (0.8 mg/ml), chased for 5 min and fixed. Total fluorescence of the cells was measured and normalized with respect to the fluorescence in untreated cells and is presented as fraction of I-switch internalised. FIG. 12a shows that the I-switch is clearly competed out in the presence of excess mBSA. Since early endosomes associated with the ALBR pathway are Rab-5 positive, we investigated I-switch (BODIPY® TMR-ALEXA FLUOR™ 647) internalization in hemocytes expressing Rab-5 GFP. Colocalization of I-switch with Rab-5 GFP confirmed its internalization through the ALBR pathway (FIG. 12b). Next, the fate of internalised I-switch at the 2 h time point was investigated by staining lysosomes with LYSO TRACKER RED™. Colocalization of dual labeled I-switch (Alexa-488/647 labeled) with LYSO TRACKER RED™ was observed indicating that the I-switch accumulates in these highly acidic organelles by the 2 h time point (FIG. 12c). Taken together, this data indicates that the I-switch is capable of marking the entire cycle of the ALBR endocytic pathway in *Drosophila* hemocytes.

Figure 3:
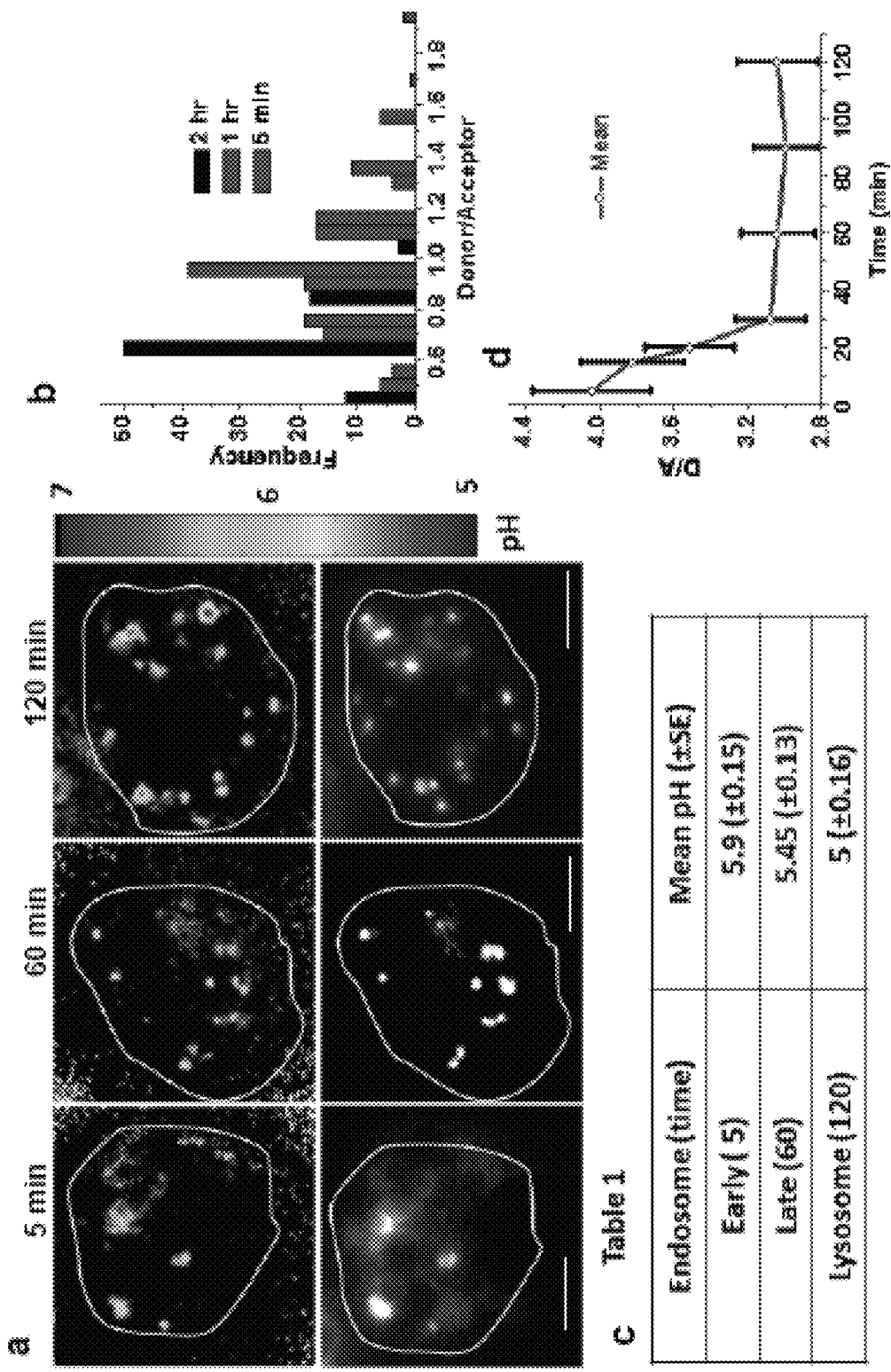
FIG. 3 shows spatio-temporal mapping of pH changes during endocytosis using the I-switch in living cells.
Figure 13:
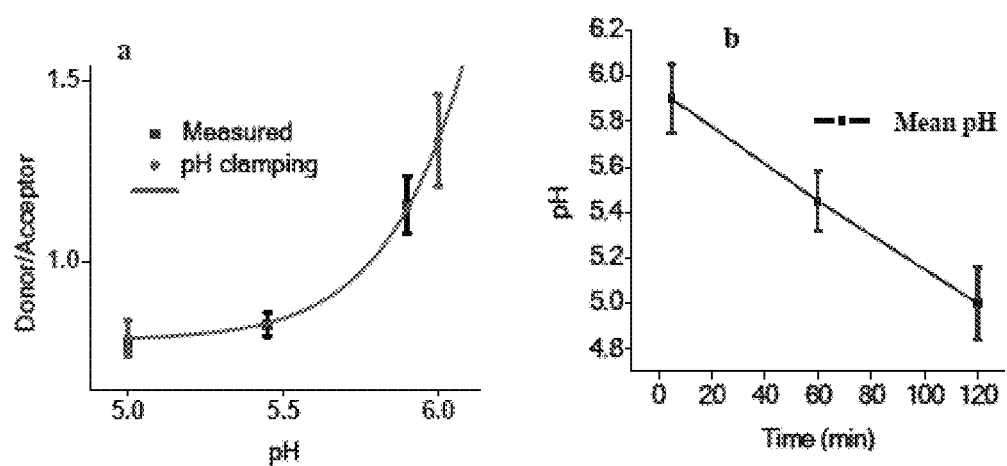
FIG. 13a is an enlarged view of intracellular standard curve to show measured pH during endocytosis.
FIG. 13b is a graph of the mean D/A of endosomes at different chase times (t=5, 60 and 120 min) converted to their respective mean pH values and plotted as a function of chase time (t). Error bar: Mean±s.e.m

This was re-affirmed by colocalization of the I-switch (BODIPY® TMR-ALEXA FLUOR™ 647) with Rab5-GFP (FIG. 2d) which marks early endosomes. We exploited the ratiometric fluorescence property of the I-switch to determine the pH of endosomes along the ALBR pathway. First, an intracellular standard curve was generated by clamping the pH of endosomes marked with ALEXA FLUOR™ 488/ALEXA FLUOR™ 647 labeled I-switch to that of an externally added buffer containing nigericin at high $K^+$ ion concentration. Nigericin is a potassium-H+ antiporter which exchanges protons and depletes pH gradients inside cells, making endosomal pH the same as the pH of the external buffer added to the cells. D/A ratio of endosomes in *Drosophila* hemocytes at desired pH were measured and plotted with respect to pH. Intracellularly, a sigmoidal increase in D/A ratio curve was obtained with a 5 fold increase from closed to open states (FIG. 2a). When this D/A curve was overlayed with the in vitro curve it recapitulated qualitatively and quantitatively its closing and opening characteristics inside cells. D/A value of each endosome was collected and presented in a histogram (FIG. 3b) and from that mean D/A was calculated at 5 min, 1 h and 2 h, compared with the standard curve in order to obtain pH at early, late and lysosomes respectively (FIG. 13b). As expected, endosomes at t=5 min are mildly acidic and progressively acidify over time. The I-switch can also be used to visualize pH changes in real time. We could capture a rapid acidification early in the endosomal maturation process from real-time pH measurements (FIG. 3d) where a sharp decrease in D/A is observed over a period of 30 min followed by a slower decrease over 2 h suggesting that early endosomes in this pathway rapidly acidify to form the late endosome that then slowly matures to the lysosome. Thus, the I-switch reports spatio-temporal pH changes efficiently and in real-time where variation in pH is a well defined correlate of molecular processes associated with endosome maturation.

Example 4

Figure 4:
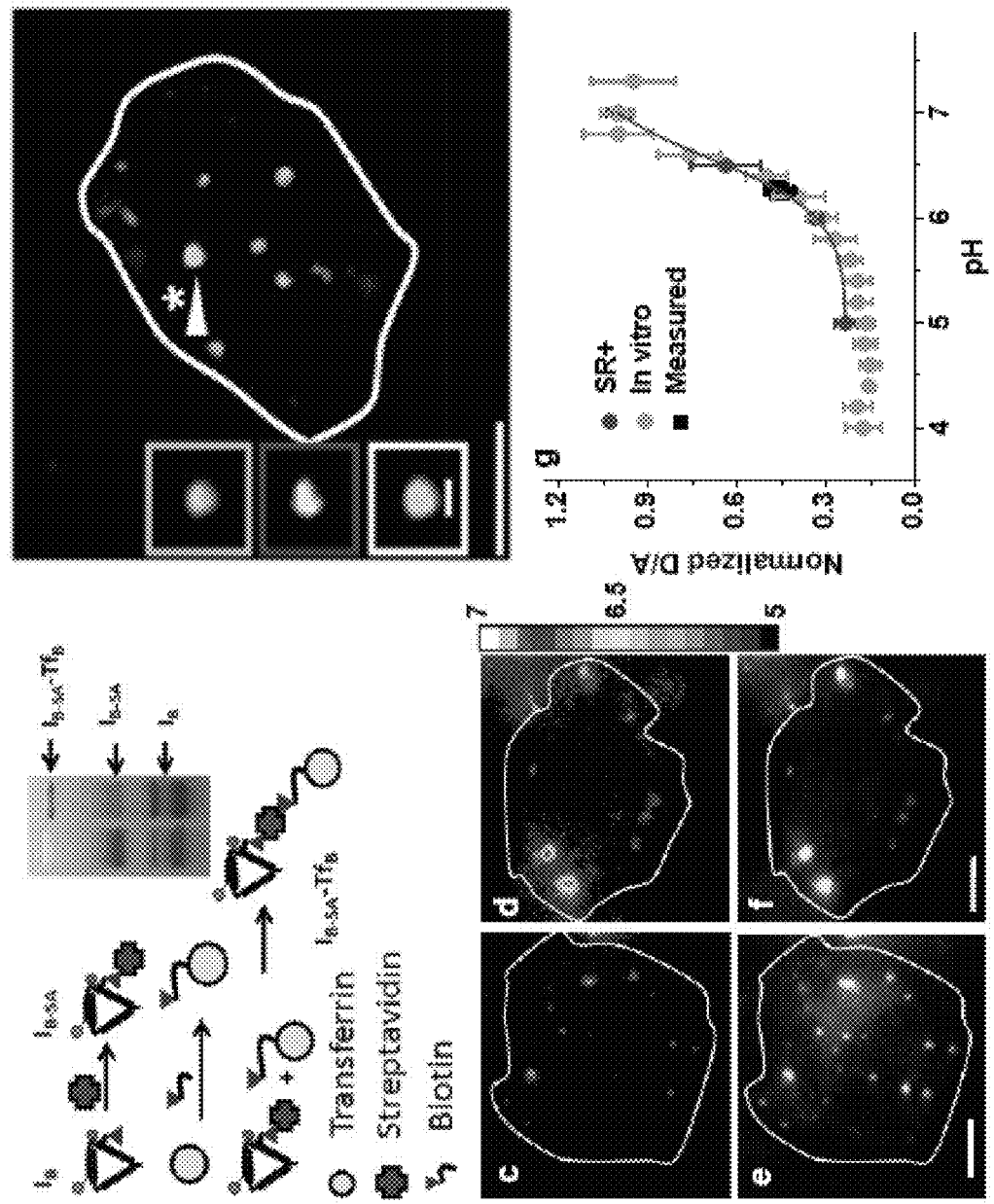
FIG. 4a shows the tagging strategy to label a specific endocytic pathway with the I-switch (ALEXA FLUOR™ 488/647). Inset: 3% Agarose-TAE gel showing the I-switch-SA conjugate ($I_{B-SA}$) and the I-switch-SA-Transferrin conjugate ($I_{BSA}$-$Tf_B$).
FIG. 4b shows Drosophila SR+ cells pulsed together with I-switchylated-transferrin ($I_{B-SA}$-$Tf_B$) and ALEXA FLUOR™ 568 labeled Transferrin ($Tf_{A568}$) Colocalization of $I_{B-SA}$-$Tf_B$ and $Tf_{A568}$ indicates internalization by Transferrin RME pathway.
FIG. 4c shows pH maps of $I_{B-SA}$-$Tf_B$ labeled endosomes in SR+ cells after a 20 min pulse
FIG. 4d is an image of similarly labeled cells after elevation to pH 7 by addition of 10 µM Nigericin.
FIG. 4e and FIG. 4f are corresponding intensity images of respective cells in the donor channel.
FIG. 4g is a graph of pH measurements in recycling endosomes. The standard curve in SR+ cells was overlayed with the in vitro curve. Also shown is the experimentally determined pH in recycling endosomes (square). Values are the mean of two independent experiments±s.e.m. Scale Bar: 5 µm. Inset: 1 µm.

Tagging the I-Switch to a Given Protein and Tracking pH Changes in its Environment In order to make the I-switch amenable as a FRET-based sensor of spatio-temporal pH changes in the environment of a protein of interest, it is possible to tag it to any given biotinylated protein. Proof of concept was demonstrated by marking the receptor mediated endocytic (RME) pathway of transferrin in *Drosophila* SR+ cells by tagging the I-switch to Transferrin (FIG. 4a). Biotinylated I-switch (IB) was first conjugated to Streptavidin (SA) which was subsequently conjugated to biotinylated Transferrin ($Tf_B$) to yield Transferrin-modified I-switch ($I_{B-SA}$-$Tf_B$) (FIG. 4a).

Figure 14:
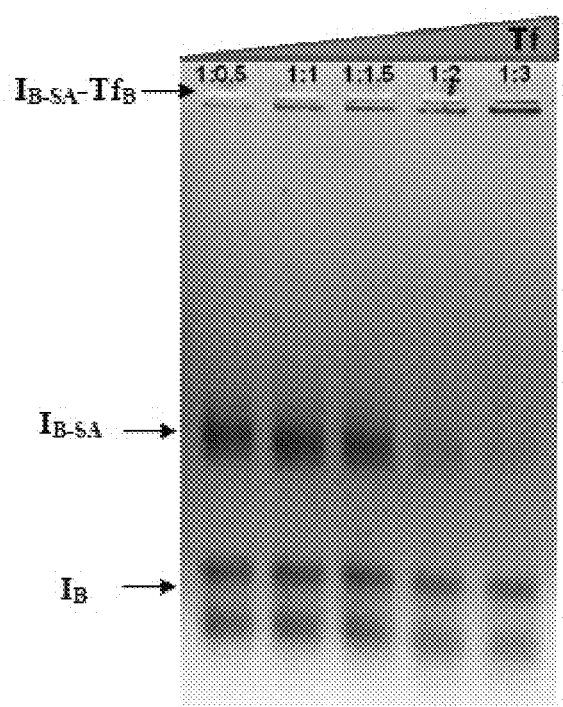
FIG. 14 is a photograph of the results of an electrophoretic mobility shift assay showing complexation of Streptavidin conjugated I-switch ($I_{B-SA}$) with Biotinylated Transferrin ($Tf_B$).

The Transferrin-modified I-switch was characterized by gel electrophoresis and size exclusion chromatography. Formation of IB-SA and IB-SA-TFB conjugate was confirmed by 3% Agarose gel (FIG. 14). Upon Streptavidin (SA) conjugation, the band corresponding to the I-switch shifts to a slower migrating species (IB-SA). To a solution of IB-SA (25 pmole) Biotinylated human holo-Transferrin (TfB) was added in varying ratios, incubated at room temperature for 1 h and then excess Biocytin was added to prevent aggregation, which was further confirmed by gel electrophoresis. With increasing TfB, the gradual increase of a slow moving band (IB-SA-TfB) was observed near the well with a concomitant disappearance of IB-SA (FIG. 14). Best results were obtained when ratio of IB:SA:TfB was 1:1:2. Further increase of TfB led to turbidity.

Size exclusion chromatography was performed on a Shimadzu HPLC system using an SEC column BioSep-SEC-S3000 (Phenomenex, with 5 μm beads, column dimensions: 300 mm×4.6 mm, total column volume (Vc)=4.98 mL, measured void volume (Vo)=1.9 mL). It is a hydrophilic bonded Silica based column with a pore size of 29 nm, and has exclusion limits of 15 kDa-700 kDa. $I_B$, $I_{B\text{-}SA}$ and $I_{B\text{-}SA}$-$Tf_B$ was prepared as described earlier, diluted to 1 μM concentration with PBS prior to injection and eluted with an isocratic flow of PBS over 30 mins. For $I_B$, SA and $I_{B\text{-}SA}$ absorbance at 260 nm was followed whereas Transferrin and its conjugates were followed with at the 475 nm absorbance characteristic of transferrin to determine heterogeneity in the $I_{B\text{-}SA}$-$Tf_B$ conjugate.

Figure 15:
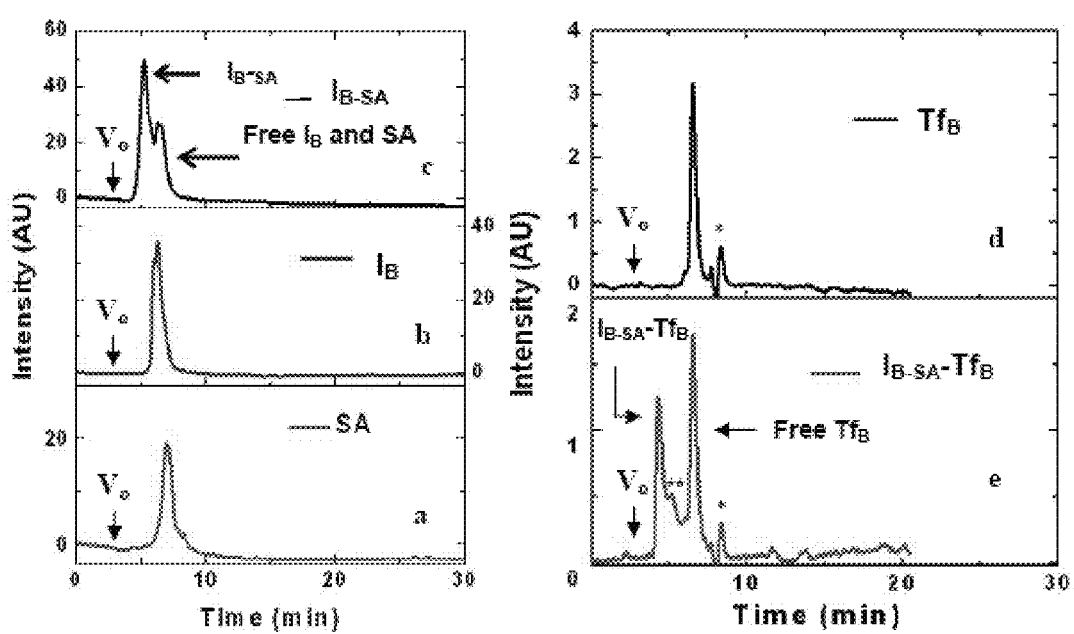
FIG. 15 is a series of charts showing the results of size exclusion chromatography (SEC) established complex stoichiometry. SEC chromatogram of Streptavidin (SA) (FIG. 15a) and I-switch ($I_B$) (FIG. 15b) showing single peaks whereas 1:1 complex of SA and $I_B$ showing two peaks of $I_{B-SA}$ and $I_B$ correspondingly (FIG. 15c).

Pure $I_B$ and pure SA showed single peaks with a retention time (Rt) of 6.2 min and 7 min respectively (FIG. 15a, b). In contrast, a mixture of 1:1 $I_B$:SA showed the appearance of a new peak (Rt: 5.2 min) that is assigned to 1:1 $I_{B\text{-}SA}$. In addition, peaks corresponding to free $I_B$ and free SA respectively are also seen (FIG. 15c). Notably there were no other peaks with a low Rt indicating that the complex formed between $I_{B\text{-}SA}$ is 1:1. This is consistent with gel electrophoresis data where only a single SA complexed band was observed.

Pure $Tf_B$ showed a predominant single peak around 6.6 min with a very minor peak near 8.3 min (indicated by *) that could correspond to some impurity in the procured sample (FIG. 15d). When $I_{B\text{-}SA}$ is added to $Tf_B$ in a 1:2 ratio it could result in multiple $Tf_B$ per $I_{B\text{-}SA}$. However, the SEC chromatogram at 475 nm (a wavelength where only $Tf_B$ is active) shows predominantly only a uniquely-sized species of $I_{B\text{-}SA}$ complexed $Tf_B$. If a heterogeneous population of more than one $Tf_B$ resulted, one would expect multiple peaks for this wavelength. However, FIG. 15d shows a chromatogram that has only two peaks, one corresponding to uncomplexed $Tf_B$ and another significantly faster than either of the starting components (4.3 min) which we assign as $I_{B\text{-}SA}$-$Tf_B$. There are no other significant populations corresponding to more than one $Tf_B$. Such species must be resolvable on the SEC given that the m.w. of $Tf_B$ is ~80 kDa, and indicates that the current protocol results in the formation of an $I_{B\text{-}SA}$ $Tf_B$ complex that carries one $Tf_B$ per $I_{B\text{-}SA}$, with extra $Tf_B$ left over in the soup. This is also consistent with our observation that the I-switchylated $Tf_B$ behaves similar to ALEXA FLUOR™ 568 labeled Tf in various endocytic assays. The small shoulder in the peak of $I_{B\text{-}SA}$-$Tf_B$ (indicated by **, FIG. 15c, Rt=5.2 min) probably originates from the complexation of $I_{B\text{-}SA}$ with the small impurity (*, FIG. 15c Rt=8.3 min) in the $Tf_B$ sample. Thus, this protocol results in a predominantly homogeneous I-switch-protein conjugate.

Drosophila SR+ cells were incubated with $I_{B\text{-}SA}$-$Tf_B$ (ALEXA FLUOR™ 488/ALEXA FLUOR™ 647 labeled $I_B$) on ice for 15 min, chased for 10 min, followed by stripping surface-bound probe using a low-pH stripping buffer, fixed and then imaged. Overlaying donor and acceptor images showed colocalization in discrete punctate structures. These were completely absent in control cells pulsed with the I-switch lacking $Tf_B$. To check the identity of these endosomes, cells were pulsed with a mixture of $I_{B\text{-}SA}$-$Tf_B$ and $Tf_{A568}$ (Transferrin labeled with ALEXA FLUOR™ 568) in a 1:1 ratio. Significant co-localization (85%) between $I_{B\text{-}SA}$-$Tf_B$ and $Tf_{A568}$ (FIG. 4b), confirmed that $I_{B\text{-}SA}$-$Tf_B$ indeed marked endosomes of the transferrin receptor mediated pathway.

Figure 16:
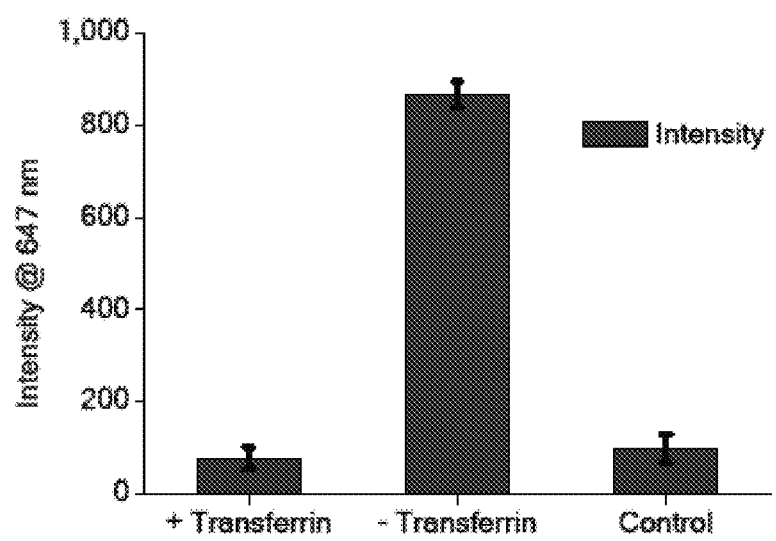
FIG. 16 is a graph showing competition studies with unlabeled Transferrin (Tf) and demonstrates that I-switch conjugated to Transferrin ($I_{B-SA}$-$Tf_B$) is internalized via transferrin receptors.

This was further confirmed by competition experiments with unlabeled Transferrin (FIG. 16). Internalization of $I_{B\text{-}SA}$-$Tf_B$ via transferrin receptor pathway was further confirmed by competition studies with excess unlabeled Transferrin. Briefly, human holo Transferrin, Tf (100 μg) was bound with transferrin receptor expressed in Drosophila SR+ cells on ice for 15 min and then chased for another 15 min in presence of I-switchylated transferrin ($I_{B\text{-}SA}$-$Tf_B$), stripped to remove any surface bound probe, fixed and imaged in a widefield microscope using a 20× objective. 100 cells per view were quantified. Total intensity of each cell in ALEXA FLUOR™ 647-channel was presented as a mean±s.e.m of two different experiments.

Transferrin marks recycling endosomes that are comparatively less acidic to the late endosome and lysosome. FIGS. 4c and d show FRET maps of recycling endosomes marked with $I_{BSA}$-$Tf_B$ at t=20 min before (FIG. 4c) and after (FIG. 4d) addition of Nigericin. The fold increase of D/A value (Blue (pH 5) to red (pH 7) (FIG. 4d) was used to quantify the acidity in these organelles. Prior to quantification, a pH calibration curve of $I_{B\text{-}SA}$-$Tf_B$ was generated in this cell line as described earlier which was shown to overlap with the in vitro pH curve (FIG. 4g) indicating that the pH sensing capability of the I-switch is unchanged after conjugation. When the D/A values of each endosome (n~50) was quantified and compared with the standard curve, it revealed a mean pH of 6.3±0.1 (FIG. 4g, Black Square) which is consistent with the mildly acidic nature of recycling endosomes. This reveals that the I-switch is a high performance reporter that, through protein conjugation, can enable measurement of its environmental pH.

Example 5

Visualizing pH Changes in Cells and Tissues of Whole Organisms

Figure 17A:
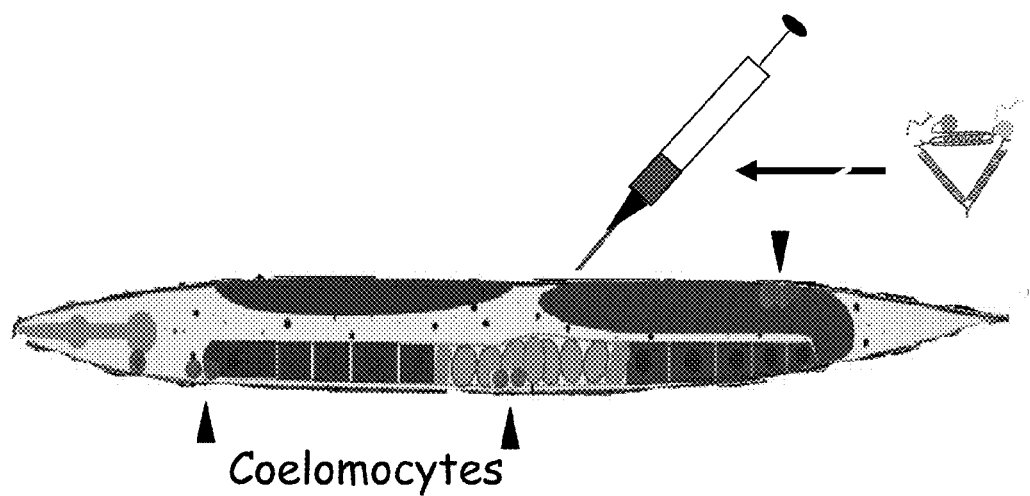
FIG. 17a is a schematic diagram showing the injection of the I-switch into C. elegans.
Figure 17B:
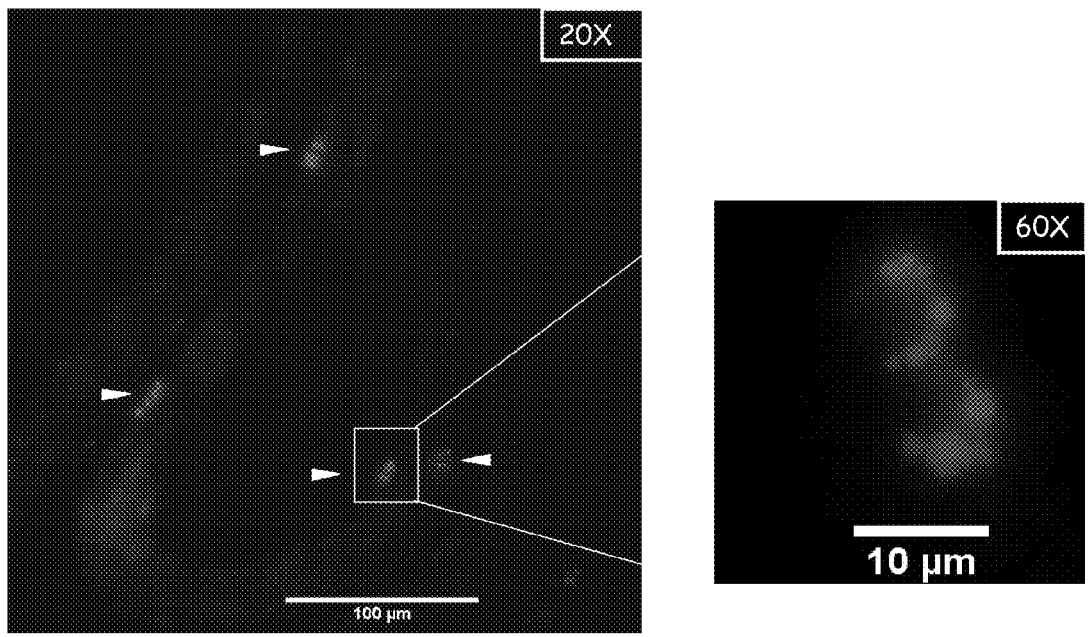
FIG. 17b is a micrograph showing the localization of the I-switch to the coelomocytes of C. elegans.

In order to test the ability of the I-switch to detect pH changes in whole organisms, the I-switch was injected into C. elegans. Briefly, the I-switch solution of Example 1 was injected into C. elegans (FIG. 17a). The sensor was found to localize to the coelomocytes of the organism, where it is endocytosed. Once localized to the endosomes, a conformational shift in the I-switch results in significant fluorescence clearly marking the endosomes in the coelomocytes of C. elegans (FIG. 17b). Accordingly, the I-switch can be used to visualize the pH changes of tissues and cellular compartments within a living organism. Moreover, by attaching the appropriate tag or targeting moiety to the I-switch, it may be possible to target the I-switch to various tissues or cell-types, such as neurons. As such, the I-switch is useful in the claimed methods to measure the pH of tissues and cells in whole organisms.

Example 6

Comparison of Unimolecular and Bimolecular I-Switches

Alternative designs for the I-switch were investigated. In particular, a bimolecular design where the I-switch is formed by two C-rich strands coming together was compared to a design with a unimolecular i-motif forming C-rich strand (partnered with another strand with mismatches). Thus, the partner strand is only marginally stable at pH 7 and detaches from the duplex when the i-motif forming strand folds into an i-motif.

Figure 18:
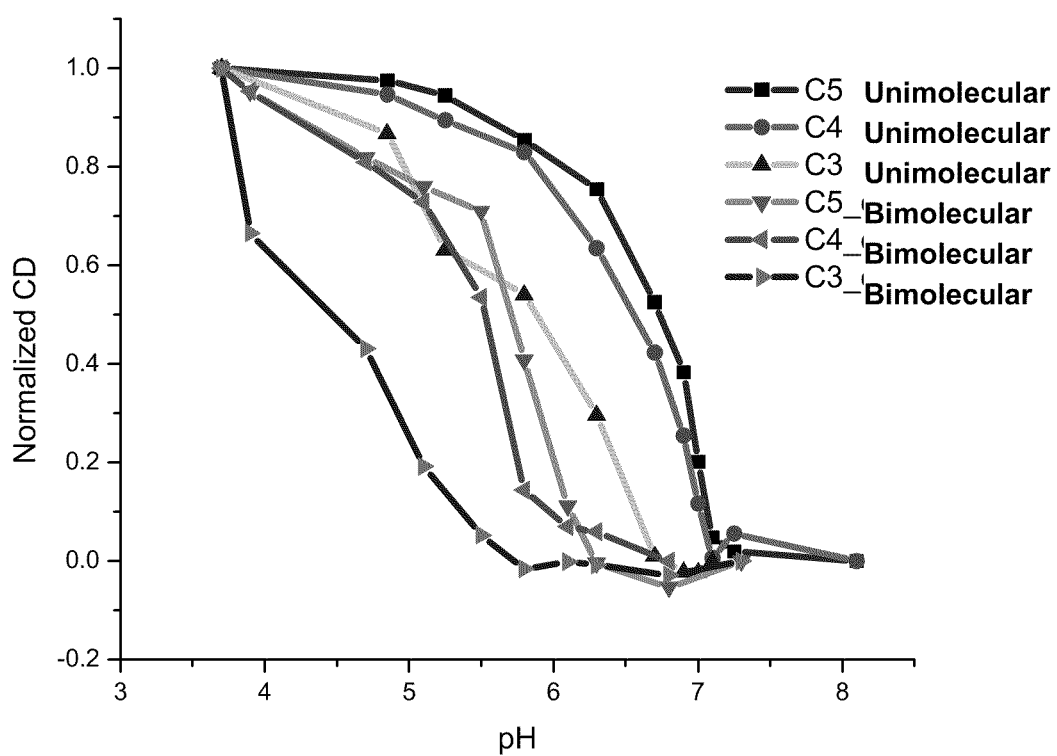
FIG. 18 is a chart showing the normalized CD data for unimolecular and bimolecular configurations of the I-switch having a range of cytosine residues in the i-motif forming sequences.

The dynamics of the I-switch over a range of pH was compared among I-switches having a variable number of cytosine residues in the two different configurations (See FIG. 18). CD spectroscopy showed that the range of pH detection may be modulated by changing the number of cytosine residues. Generally, increasing the number of cytosine residues from 3-5 shifted the limits of detecting to a higher pH for both the bimolecular and the unimolecular I-switch. When the unimolecular I-switch is used, the pH can be detected at lower regimes compared to the bimolecular I-switch. Accordingly, these results demonstrate that the I-switch of the invention is useful in methods for detecting pH changes over a biologically-important range of values.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

What is claimed is:

1. A method for determining the internal pH of a cell or an internal region thereof comprising:

contacting the cell or internal region thereof with one or more indicators having at least two i-motif forming sequences, wherein the two i-motif forming oligonucleotides have the sequence of SEQ ID NO: 1 and SEQ ID NO: 2, and wherein the one or more indicators become internalized in the cell, wherein one or more first i-motif forming sequences are labeled with a first member of a label pair and one or more second i-motif forming sequences are labeled with a second member of a label pair, wherein the one or more first i-motif forming sequences and the one or more second i-motif forming sequences form one or more i-motifs in response to exposure to one or more pH conditions within the cell or internal region thereof such that the first and second members of the label pair interact; and detecting the presence, absence, or magnitude of a signal from the interacting label pair to determine the internal pH of the cell or internal region thereof.

2. The method of claim 1, wherein the at least two i-motif forming sequences form an i-motif having two parallel-stranded C—H.C$^+$ base paired duplexes that are intercalated in an anti-parallel orientation.

3. The method of claim 1, wherein the i-motif is formed under acidic conditions.

4. The method of claim 1, wherein the i-motif dissociates under neutral or basic conditions.

5. The method of claim 1, wherein the at least two i-motif forming sequences are present in the same oligonucleotide.

6. The method of claim 1, wherein the at least two i-motif forming sequences are in at least two separate oligonucleotides.

7. The method of claim 6, wherein the at least two separate oligonucleotides are partially complementary to a third oligonucleotide.

8. The method of claim 7, wherein the third oligonucleotide has the sequence of SEQ ID NO: 3.

9. The method of claim 1, wherein the interacting label pair comprises donor and acceptor moieties.

10. The method of claim 1, wherein the detecting the presence, absence, or magnitude of a signal includes determining a donor/acceptor (D/A) signal ratio.

11. The method of claim 9, wherein the donor moiety is selected from the group consisting of fluorescein, dilithium 4-carboxy-2-(3,6-diamino-4,5-disulfonatoxanthenium-9-yl) benzoate (ALEXA FLUOR™ 488), and 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TMR).

12. The method of claim 9, wherein the acceptor moiety is selected from the group consisting of rhodamine, eosin, erythrosin, (3E)-9-{2-[(4-{[2,5-dioxo-1-pyrrolidinyl)oxy]carbonyl}-1-piperidinyl)sulfonyl]phenyl}-N-methyl-6-[methyl(phenyl)amino]-N-phenyl-3H-xanthen-2-iminium chloride (QSY-7™, (2Z)-3-[6-[5-[[2-[(E)-[(2R,3S,5S,8S,9S,10R,13S,14S,17R)-17-[(2S,3R,4R,5S)-3,4-dihydroxy-5,6-dimethylheptan-2-yl]-2,3-dihydroxy-10,13-dimethyl-1,2,3,4,5,7,8,9,11,12,14,15,16,17-tetradecahydrocyclopenta[alphenanthren-6-ylidene]amino]oxyacetyl]amino]pentylamino]-6-oxohexl]-2-[(2E,4E)-5-[3,3-dimethyl-5-sulfo-1-(3-sulfopropyl)indol-1-ium-2-yl]penta-2,4-dienylidene]-3-methyl-1-(3-sulfopropyl)indole-5-sulfonic acid (ALEXA FLUOR™ 647), 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TMR), 2-[(E,3Z)-3-(1,3-dihydroindol-2-ylidene)prop-1-enyl]-3H-indol-1-ium (CY3™), and 5-(4-{[(2,5-dioxopyrrolidin-1-yl)oxy]carbonyl}phenyl)-2,3,3,7,7,8-hexamethyl-2,3,7,8-tetrahydro-1H-pyrano[3,2-f:5,6-f']diindole-10,12-disulfonic acid (ALEXA FLUOR™ 532).

13. The method of claim 1, wherein the interacting label pair comprises a fluorophore and a quencher.

14. The method of claim 1, wherein the detecting comprises measuring the magnitude of the signal generated, wherein the magnitude indicates the internal pH of the cell or the internal region thereof.

15. The method of claim 1, wherein the indicator further comprises a tagging moiety for linking the indicator to other biomolecules.

16. The method of claim 1, wherein the indicator further comprises one or more of a fusogenic peptide, a membrane-permeabilizing peptide, a sub-cellular localization sequence, or a cell-receptor ligand.

17. The method of claim 16, wherein the sub-cellular localization sequence targets the indicator to an internal region of the cell selected from the group consisting of: the cytosol, the endoplasmic reticulum, the mitochondrial matrix, the chloroplast lumen, the medial trans-Golgi cisternae, the lumen of lysosome, and the lumen of an endosome.

* * * * *